(12) United States Patent
Bergo

(10) Patent No.: US 11,913,964 B2
(45) Date of Patent: Feb. 27, 2024

(54) MULTIPLEXED BEAD-BASED ANALYTICAL ASSAYS

(71) Applicant: Adeptrix Corp., Beverly, MA (US)

(72) Inventor: Vladislav B. Bergo, Boston, MA (US)

(73) Assignee: ADEPTRIX CORP., Beverly, MA (US)

( * ) Notice: Subject to any disclaimer, the term of this patent is extended or adjusted under 35 U.S.C. 154(b) by 295 days.

(21) Appl. No.: 17/187,388

(22) Filed: Feb. 26, 2021

(65) Prior Publication Data

US 2021/0389333 A1 Dec. 16, 2021

Related U.S. Application Data

(60) Provisional application No. 62/982,126, filed on Feb. 27, 2020.

(51) Int. Cl.

| | | |
|---|---|---|
| *G01N 33/68* | (2006.01) | |
| *G01N 21/33* | (2006.01) | |
| *G01N 21/64* | (2006.01) | |
| *G01N 33/52* | (2006.01) | |
| *C07C 309/65* | (2006.01) | |
| *C07C 309/73* | (2006.01) | |
| *A01N 1/02* | (2006.01) | |
| *G01N 1/40* | (2006.01) | |
| *G01N 33/543* | (2006.01) | |

(52) U.S. Cl.
CPC ... *G01N 33/6896* (2013.01); *G01N 33/54306* (2013.01); *G01N 33/54313* (2013.01); *G01N 2333/435* (2013.01); *G01N 2560/00* (2013.01)

(58) Field of Classification Search
CPC ......... G01N 33/6896; G01N 33/54306; G01N 33/54313; G01N 2333/435; G01N 2560/00; G01N 33/6848
See application file for complete search history.

(56) References Cited

U.S. PATENT DOCUMENTS

| | | |
|---|---|---|
| 9,618,520 B2 | 4/2017 | Bergo |
| 10,101,336 B2 | 10/2018 | Bergo |
| 10,451,631 B2 | 10/2019 | Bergo |
| 11,131,674 B2 | 9/2021 | Bergo |
| 2009/0023158 A1 | 1/2009 | Shapiro et al. |
| 2009/0270278 A1 | 10/2009 | Lim et al. |
| 2010/0256015 A1 | 10/2010 | Lim et al. |
| 2010/0317542 A1 | 12/2010 | Lim et al. |

(Continued)

OTHER PUBLICATIONS

Misiti, Francesco, M. Elisabetta Clementi, and Bruno Giardina. "Oxidation of methionine 35 reduces toxicity of the amyloid beta-peptide (1-42) in neuroblastoma cells (IMR-32) via enzyme methionine sulfoxide reductase A expression and function." Neurochemistry international 56.4 (2010): 597-602. (Year: 2010).*

(Continued)

*Primary Examiner* — Jennifer Wecker
*Assistant Examiner* — Oyeleye Alexander Alabi
(74) *Attorney, Agent, or Firm* — KRIEGSMAN & KRIEGSMAN

(57) ABSTRACT

Bead-based analytical assays suitable for detecting changes in the abundance of target analytes in biological samples are disclosed. In an embodiment, an assay involves incubating a sample with one or several beads that are capable of binding several distinct analytes in an amount sufficient for detection by mass spectrometry from a single bead.

17 Claims, 20 Drawing Sheets

Specification includes a Sequence Listing.

(56) References Cited

U.S. PATENT DOCUMENTS

| | | |
|---|---|---|
| 2012/0077688 A1 | 3/2012 | Bergo et al. |
| 2012/0087940 A1 | 4/2012 | Inoue et al. |
| 2012/0202709 A1 | 8/2012 | Bergo |
| 2013/0224287 A1* | 8/2013 | Reis .................. A61P 25/28 424/140.1 |
| 2014/0037658 A1 | 2/2014 | Nilsson et al. |
| 2014/0235471 A1 | 8/2014 | Bergo et al. |
| 2014/0323330 A1 | 10/2014 | Bergo |
| 2016/0008785 A1 | 1/2016 | Bergo |
| 2017/0176453 A1 | 6/2017 | Bergo |
| 2017/0219601 A1 | 8/2017 | Bergo |
| 2019/0004038 A1 | 1/2019 | Bergo |
| 2019/0072546 A1 | 3/2019 | Bergo |
| 2019/0219578 A1* | 7/2019 | Mitsuhashi .......... G01N 33/543 |
| 2019/0376984 A1* | 12/2019 | Kidd .................. G01N 33/52 |
| 2021/0018513 A1 | 1/2021 | Bergo |
| 2021/0190773 A1 | 6/2021 | Bergo |
| 2021/0389333 A1 | 12/2021 | Bergo |
| 2022/0128570 A1 | 4/2022 | Bergo |

OTHER PUBLICATIONS

Misiti et al., "Oxidation of methionine 35 reduces toxicity of the amyloid beta-peptide(1-42) in neuroblastoma cells (IMR-32) via enzyme methionine sulfoxide reductase A expression and function," Neurochemistry International, 56(4):597-602 (2010).

International Search Report dated Jun. 9, 2021, for PCT Application No. PCT/US21/20016.

Written Opinion dated Jun. 9, 2021, for PCT Application No. PCT/US21/20016.

* cited by examiner

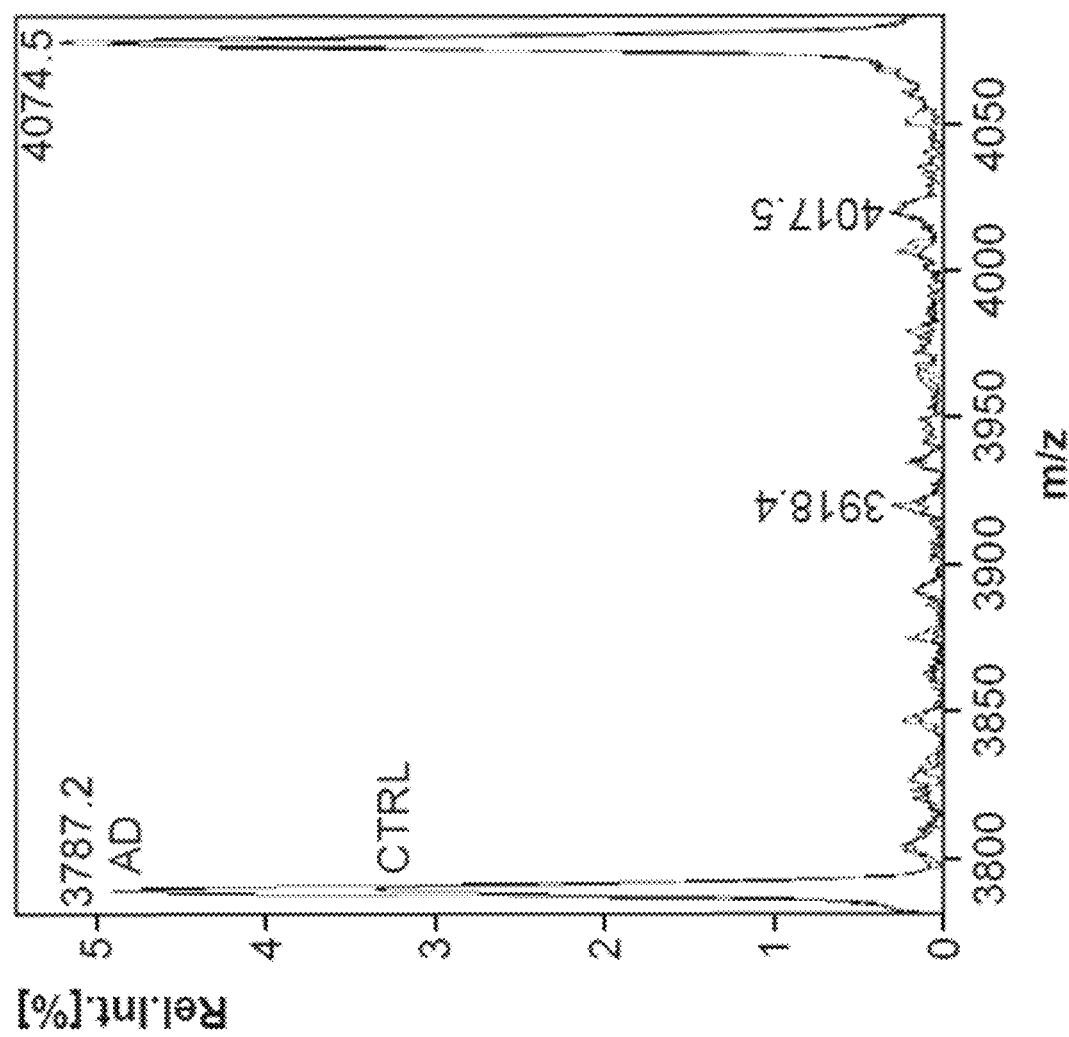

MULTIPLEXED BEAD-BASED ANALYTICAL ASSAYS

RELATED APPLICATIONS

The present application claims the benefit under 35 U.S.C. 119(e) of U.S. Provisional Patent Application No. 62/982,126, inventor Vladislav B. Bergo, filed Feb. 27, 2020, the disclosure of which is incorporated herein by reference.

SEQUENCE LISTING

The instant application contains a Sequence Listing which has been submitted electronically in ASCII format and is hereby incorporated by reference in its entirety. Said ASCII copy, created on Feb. 19, 2021, is named 84306A_SL.txt and is 10,898 bytes in size.

FIELD

The embodiments disclosed herein relate generally to bead-based assays and more specifically to measuring analytes in biological samples using bead-based assays. The embodiments disclosed herein also relate to proteomics, protein quantification, post-translational modifications of proteins, affinity separations, microarrays and mass spectrometry.

BACKGROUND

Detection, identification and quantification of multiple analytes in biological samples is an important area of basic and applied biology. In many applications, the analytes are proteins and/or protein fragments, such as proteolytic peptides produced by enzymatic digestion of precursor proteins. Mass spectrometry (MS) is the key analytical platform for quantitative analysis of proteins and peptides.

Recently there has been considerable progress in developing quantitative MS-based methods that utilize detection from individual beads or microspheres. One example of such approach, termed "immuno-MALDI" or "iMALDI" is described in the U.S. Pat. No. 7,846,748 and several publications. The iMALDI approach is generally limited to detecting a single analyte. On the other hand, recent U.S. Pat. No. 9,618,520 and U.S. patent application Ser. No. 13/369,939, Publication No. US 2012-0202709 A1 describe various quantitative bead-based methods, which are multiplexed, that is capable of measuring multiple distinct analytes.

Developing bead-based MS assays is often associated with challenges such as optimizing the analyte binding capacity of individual beads and of the entire bead array, creating conditions for depleting one or more analytes from a sample and detecting the bead-captured analytes with sufficient sensitivity.

Accordingly, there is still a need for methods and compositions that will enable analysis of proteins and peptides by MS in a bead array format.

SUMMARY

In one aspect, the present specification describes methods of measuring a sample by capturing multiple analytes from the sample on a single bead and analyzing the single bead by MS. The described methods enable measuring multiple amyloid beta (Aβ) peptides in human cerebrospinal fluid (CSF) and other biofluids including Aβ1-6, Aβ1-7, Aβ1-8, Aβ1-9, Aβ1-10, Aβ1-11, Aβ1-21, Aβ1-22, Aβ1-23, Aβ1-24, Aβ1-25, Aβ1-26, Aβ1-31 and Aβ1-32, as well as Aβ1-12, Aβ1-13, Aβ1-14, Aβ1-15, Aβ1-16, Aβ1-17, Aβ1-18, Aβ1-19, Aβ1-20, Aβ1-27, Aβ1-28, Aβ1-29, Aβ1-30, Aβ1-33, Aβ1-34, Aβ1-35, Aβ1-36, Aβ1-37, Aβ1-38, Aβ1-39, Aβ1-40, Aβ1-42 and Aβ1-43. Distinct Aβ peptides have significantly different abundance in the sample.

In another aspect, the present specification describes a bead array, in which distinct reactive sites contain distinct capture agents that specifically recognize and bind a same target, e.g. an amyloid beta peptide.

In yet another aspect, the present specification describes a method of analyzing a sample. The method includes capturing a first target from an undigested biological sample, enzymatically digesting an unreacted portion of the sample and subsequently capturing a distinct second target from the digested sample. A proteolytic fragment of the first target may be also captured from the digested sample.

In yet another aspect, the present specification describes methods of classifying a biological sample according to a signal from an Aβ peptide in a mass spectrum that is obtained from a single reactive site of a bead array. The biological sample is obtained from a human or a non-human subject.

The methods and compositions described in this specification may be utilized to analyze various biological samples, including cell-free protein transcription-translation reactions, bacterial cells, mammalian cells, cell culture supernatants, animal models, xenografts, tissue biopsies, biofluids such as serum, plasma and cerebrospinal fluid, and others. The described methods and compositions may be utilized in a broad range of applications including basic research, pharmaceutical drug discovery and drug development, disease diagnostics and prognostics, biomarker discovery and validation, personalized medicine, precision medicine, systems biology and others.

DESCRIPTION OF FIGURES

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

FIG. 1A schematically depicts an affinity binding reaction, in which a sample contains at least a first peptide and a second peptide and a binding capacity of a bead array is lower than a combined amount of the first peptide and the second peptide in the sample.

FIG. 1B schematically depicts an affinity binding reaction, in which a sample contains at least a first peptide and a second peptide and a bead array contains a reactive site that specifically binds the first peptide and the second peptide, and a reactive site that specifically binds the first peptide and not the second peptide.

FIG. 1C schematically depicts an affinity binding reaction, in which samples that contain different amounts of a first peptide and a second peptide are incubated with distinct bead arrays.

FIG. 1D schematically depicts an affinity binding reaction, in which a sample is incubated with a first bead array and an unreacted portion of the sample is proteolytically digested and subsequently incubated with a second bead array.

FIG. 3C is an expanded view of the mass spectra shown in FIG. 2 in the 3750-4100 m/z region.

DETAILED DESCRIPTION

Figure 1A:
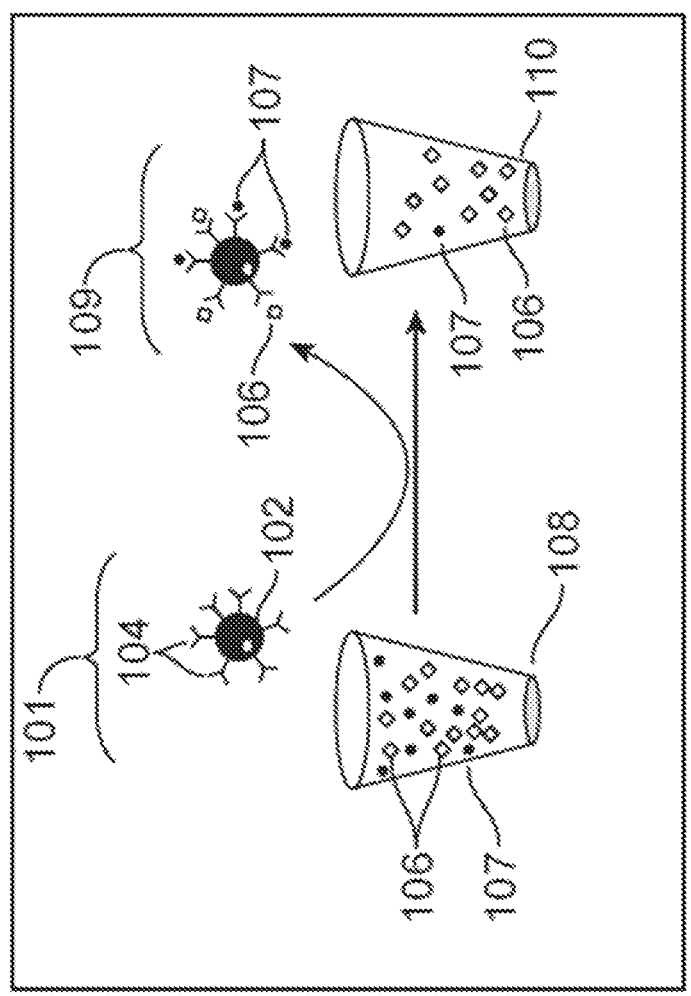
FIGS. 1A through 1D schematically depict various affinity binding reactions that include incubating a sample with a bead array.

The term "bead array" refers to a group that includes at least two reactive sites. A bead array may be located in a container, such as a microcentrifuge tube, or in a well of a multiwell plate, in which case it may be referred to as a suspension bead array.

The term "reactive site" refers to a combination of a bead and at least one capture agent that is associated with the bead. An example of a reactive site is a bead containing a covalently bound antibody.

The term "capture agent" refers to a molecule, such as an antibody, or a molecular complex that is capable of binding a compound. A singular form of the term "capture agent" may refer to a plurality of identical molecules or a plurality of identical molecular complexes. For example, it may refer to a plurality of identical antibody molecules.

The terms "target analyte" and "target" are used interchangeably throughout the instant specification and generally refer to a binding partner of a capture agent. Singular forms of the terms "target analyte" and "target" may refer to a plurality of molecules, e.g. a plurality of peptide molecules.

The terms "immunoprecipitation" and "IP" refer to a known method of capturing an antigen from a solution by using an antibody that: (i) specifically recognizes the antigen and (ii) is immobilized on a solid support. Immunoprecipitation is commonly used to purify and concentrate an antigen, such as a protein or a peptide before analyzing the antigen by one or several analytical methods. The methods disclosed in the instant specification enable immunoprecipitation to be performed on a single reactive site of a bead array.

The terms "peptide" and "polypeptide" are used interchangeably throughout the specification and refer to a combination of at least two amino acids that are linked by an amide bond, which is also known as a peptide bond.

The term "protein" is used according to its definition in the fields of biochemistry and molecular biology.

The terms "well" and "microwell" are used interchangeably throughout the instant specification and refer to a topological feature such as a pit or a depression that is able to hold a liquid medium, a particle or both.

The term "microarray" refers to a plurality of spatially separated spots that are positioned on a substantially flat surface of a solid support. Individual spots within a microarray may contain a matrix for mass spectrometry.

The term "endogenous" refers to originating from within an organism.

The terms "amyloid beta peptide" and "Aβ peptide" are used interchangeably throughout the specification and refer to a fragment of amyloid-beta precursor protein (APP). The entry number and the entry name for human APP in the Universal Protein Resource (UniProt) database are P05067 and A4_HUMAN, respectively. Aβ peptides are typically derived from a region located near the C-terminus of APP. An Aβ peptide may be of human or non-human origin.

An Aβ peptide is usually designated according to the first and the last amino acid in its sequence, with Asp672 of APP being assigned to 1. Thus, peptide Aβ1-42 refers to a peptide containing amino acids 672-713 of human APP, while peptide Aβ1-40 refers to a peptide containing amino acids 672-711 of human APP.

Table 1 below lists names, sequences and average molecular weights for peptides Aβ1-X, where X is between 6 and 43.

| Peptide | Sequence | SEQ ID NO: | Mol. weight |
|---------|----------|------------|-------------|
| Aβ1-6   | DAEFRH   | 1          | 773.80      |
| Aβ1-7   | DAEFRHD  | 2          | 888.89      |
| Aβ1-8   | DAEFRHDS | 3          | 975.97      |

-continued

| Peptide | Sequence | SEQ ID NO: | Mol. weight |
|---|---|---|---|
| Aβ1-9 | DAEFRHDSG | 4 | 1033.02 |
| Aβ1-10 | DAEFRHDSGY | 5 | 1196.20 |
| Aβ1-11 | DAEFRHDSGYE | 6 | 1325.31 |
| Aβ1-12 | DAEFRHDSGYEV | 7 | 1424.45 |
| Aβ1-13 | DAEFRHDSGYEVH | 8 | 1561.59 |
| Aβ1-14 | DAEFRHDSGYEVHH | 9 | 1698.73 |
| Aβ1-15 | DAEFRHDSGYEVHHQ | 10 | 1826.86 |
| Aβ1-16 | DAEFRHDSGYEVHHQK | 11 | 1955.03 |
| Aβ1-17 | DAEFRHDSGYEVHHQKL | 12 | 2068.19 |
| Aβ1-18 | DAEFRHDSGYEVHHQKLV | 13 | 2167.33 |
| Aβ1-19 | DAEFRHDSGYEVHHQKLVF | 14 | 2314.50 |
| Aβ1-20 | DAEFRHDSGYEVHHQKLVFF | 15 | 2461.68 |
| Aβ1-21 | DAEFRHDSGYEVHHQKLVFFA | 16 | 2532.76 |
| Aβ1-22 | DAEFRHDSGYEVHHQKLVFFAE | 17 | 2661.87 |
| Aβ1-23 | DAEFRHDSGYEVHHQKLVFFAED | 18 | 2776.96 |
| Aβ1-24 | DAEFRHDSGYEVHHQKLVFFAEDV | 19 | 2876.09 |
| Aβ1-25 | DAEFRHDSGYEVHHQKLVFFAEDVG | 20 | 2933.15 |
| Aβ1-26 | DAEFRHDSGYEVHHQKLVFFAEDVGS | 21 | 3020.22 |
| Aβ1-27 | DAEFRHDSGYEVHHQKLVFFAEDVGSN | 22 | 3134.33 |
| Aβ1-28 | DAEFRHDSGYEVHHQKLVFFAEDVGSNK | 23 | 3262.50 |
| Aβ1-29 | DAEFRHDSGYEVHHQKLVFFAEDVGSNKG | 24 | 3319.55 |
| Aβ1-30 | DAEFRHDSGYEVHHQKLVFFAEDVGSNKGA | 25 | 3390.63 |
| Aβ1-31 | DAEFRHDSGYEVHHQKLVFFAEDVGSNKGAI | 26 | 3503.79 |
| Aβ1-32 | DAEFRHDSGYEVHHQKLVFFAEDVGSNKGAII | 27 | 3616.95 |
| Aβ1-33 | DAEFRHDSGYEVHHQKLVFFAEDVGSNKGAIIG | 28 | 3674.00 |
| Aβ1-34 | DAEFRHDSGYEVHHQKLVFFAEDVGSNKGAIIGL | 29 | 3787.16 |
| Aβ1-35 | DAEFRHDSGYEVHHQKLVFFAEDVGSNKGAIIGLM | 30 | 3918.36 |
| Aβ1-36 | DAEFRHDSGYEVHHQKLVFFAEDVGSNKGAIIGLMV | 31 | 4017.49 |
| Aβ1-37 | DAEFRHDSGYEVHHQKLVFFAEDVGSNKGAIIGLMVG | 32 | 4074.54 |
| Aβ1-38 | DAEFRHDSGYEVHHQKLVFFAEDVGSNKGAIIGLMVGG | 33 | 4131.59 |
| Aβ1-39 | DAEFRHDSGYEVHHQKLVFFAEDVGSNKGAIIGLMVGGV | 34 | 4230.72 |
| Aβ1-40 | DAEFRHDSGYEVHHQKLVFFAEDVGSNKGAIIGLMVGGVV | 35 | 4329.86 |
| Aβ1-41 | DAEFRHDSGYEVHHQKLVFFAEDVGSNKGAIIGLMVGGVVI | 36 | 4443.02 |
| Aβ1-42 | DAEFRHDSGYEVHHQKLVFFAEDVGSNKGAIIGLMVGGVVIA | 37 | 4514.10 |
| Aβ1-43 | DAEFRHDSGYEVHHQKLVFFAEDVGSNKGAIIGLMVGGVVIAT | 38 | 4615.20 |

In an embodiment, the instant specification describes a method for binding multiple peptides, such as amyloid beta peptides from a sample using affinity capture on a reactive site of a bead array followed by MS detection of the captured peptides individually from the reactive site. The described method is useful for measuring changes in the abundance for one or multiple peptide analytes in two or more samples.

In reference to FIG. 1A, a sample 108 contains at least a first peptide 107 and a second peptide 106 that is structurally distinct from the first peptide. The sample is brought in contact with a bead array, which contains a reactive site 101. The reactive site contains a bead 102 and a capture agent 104 that specifically recognizes the first peptide and the second peptide. Contacting the sample with the bead array causes the first peptide and the second peptide to bind to the reactive site and therefore to the bead array. The binding capacity of the bead array may be lower than a combined amount of the first and the second peptides in the sample. Accordingly, at least some amount of the first peptide 107 and the second peptide 106 remains in the sample 110 after the contacting step. The duration of the contacting step is selected to cause the first and the second peptides to bind to the reactive site in a ratio that is equivalent to a ratio of the first peptide to the second peptide in the sample. After the contacting step, the reacted reactive site 109 contains the bound first and second peptides, which are then released individually from the reactive site and measured using MS.

The method described above enables quantitative measurement of an abundance of the first and the second peptides that are present in the sample because a substantial amount, e.g. more than 50%, more than 60%, more than 70%, more than 80%, more than 90%, or more than 95% of the first and the second peptides from the sample is captured by the bead array and a signal from the first peptide is detected by MS along with a signal from the second peptide, so that the intensity of signal from the first peptide can be readily compared to the intensity of signal from the second peptide. When two or more samples are measured using the above-described method, a difference in the ratio of the first peptide signal to the second peptide signal between the samples is indicative of a difference in the amounts of the two peptides present in the corresponding samples.

The sample 108 may contain a cell homogenate, a tissue homogenate, a cell culture supernatant, a biofluid such as CSF, serum, plasma, etc. A volume of the biofluid, such as CSF may be not greater than 5 ml (5 milliliters), not greater than 1 ml, not greater than 0.5 ml, not greater than 0.25 ml, not greater than 0.15 ml, not greater than 0.1 ml or not greater than 0.05 ml (50 µL or 50 microliters).

The reactive site of the bead array contains a bead and a capture agent, e.g. an antibody that is preferably covalently bound to the bead. The antibody specifically recognizes an epitope that exists in the first peptide and in the second peptide. The first and the second peptides may be distinct amyloid beta peptides. The first Aβ peptide may be significantly more abundant than the second Aβ peptide, e.g. the abundance ratio of the first Aβ peptide to the second Aβ peptide may be greater than 10:1, greater than 25:1, greater than 50:1 or greater than 100:1. During the contacting step the antibody may specifically bind additional Aβ peptides from the sample, if such peptides contain the recognized epitope. This enables on-bead multiplexing and analysis of several amyloid beta peptides from a single reactive site. The number of such peptides in the sample may be greater than 5, greater than 10, greater than 20 or greater than 30.

Antibodies that recognize multiple Aβ peptides are commercially available. Examples of such antibodies include anti-β-Amyloid, 1-16 antibody, catalog #803004 from BioLegend (San Diego CA), β-Amyloid (D3D2N) mouse mAb, catalog #15126 and β-Amyloid (D54D2) XP® rabbit mAb, catalog #8243, both from Cell Signaling Technology (Danvers MA).

It is noted that due to conformational flexibility of the Aβ peptides, it may require experimental evaluation of multiple antibodies, such as multiple antibody clones, in order to identify the capture agent that has a stronger preference for a particular Aβ peptide when multiple Aβ peptides are present in the sample. For example, a specific antibody clone may have a greater preference for Aβ 1-15 peptide when multiple Aβ peptides are present in the sample. Accordingly, mass spectra obtained using different antibody clones may have different relative intensity of signals from individual Aβ peptides.

The binding capacity of a reactive site of a bead array for an analyte is defined as the maximum amount of the analyte that may specifically bind to the reactive site. If the reactive site is capable of specifically binding multiple analytes, its binding capacity is defined as the maximum combined amount of the multiple analytes that may specifically bind to the reactive site. The binding capacity of a bead array for an analyte is defined is the maximum amount of the analyte that may specifically bind to the bead array. Therefore, the binding capacity of the bead array for a particular analyte is approximately equal to the binding capacity of a single reactive site, which is capable of binding the analyte, multiplied by the number of replicate reactive sites that are present in the bead array.

The bead array may be made to have an analyte binding capacity that exceeds 1 picomole, 5 picomoles, 10 picomoles, 50 picomoles, or 100 picomoles that is sufficient for depleting low, medium and high abundance peptide and/or protein analytes from biological samples containing up to 50 milligrams (mg) or more of total input protein. The analyte binding capacity of a single reactive site in such bead array may exceed 100 femtomoles, 500 femtomoles or 1 picomole.

The duration of the contacting step, i.e. the duration of incubation of the bead array with the sample is determined, in part, by the diffusion rate of the analyte within the bead of the reactive site. For beads that are sufficiently large, e.g. have diameter that exceeds 200 microns (µm), the duration of the contacting step is preferably more than 1 hour. In some cases, the contacting step should last more than 3 hours, more than 6 hours or overnight (more than 12 hours). The duration of the contacting step may be determined by performing a time course study.

When two or more samples are analyzed using the described methods, accurate results will be obtained if it is ensured that the samples contain approximately equivalent amounts of total input protein. For analysis of liquid samples such as CSF, samples that have approximately equal volume may be assumed to have approximately equal amounts of total input protein.

In an embodiment, the instant specification describes a method for affinity capture of a peptide analyte on distinct reactive sites of a bead array, followed by MS detection of the captured analyte from individual reactive sites. The described method is useful for measuring multiple distinct Aβ peptides.

Figure 1B:
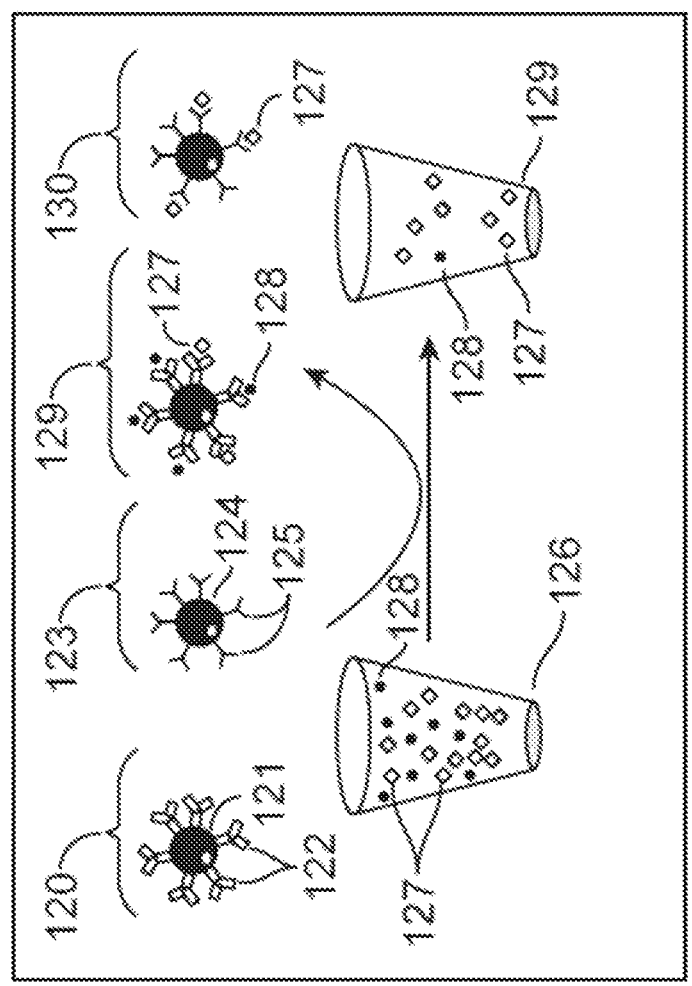

In reference to FIG. 1B, a sample 126 contains a first peptide 127 and a second peptide 128 that is distinct from the first peptide. The sample is brought in contact with a bead array, which contains a first reactive site 120 and a second reactive site 123. The first reactive site contains a bead 121 and a capture agent 122 that specifically recognizes the first peptide and the second peptide. The second reactive site contains a bead 124 and a distinct capture agent 125 that specifically recognizes the first peptide and not the second peptide. The binding capacity of the bead array may be greater than, equal to, or lower than an amount of the first peptide in the sample. The binding capacity of the bead array may be greater than, equal to, or lower than an amount of the second peptide in the sample. Contacting the sample with the bead array causes the first peptide to bind to the first and the second reactive sites and the second peptide to bind to the first reactive site and not the second reactive site. Depending upon the binding capacity of the bead array and the duration of the contacting step, the resulting sample 129 may contain an amount of the first peptide, an amount of the second peptide, or both. After the contacting step, the reacted reactive sites 129 and 130 are individually analyzed by MS. Analyzing the first reactive site 129 may be used to obtain a ratio of the first peptide to the second peptide in the reactive site.

Antibodies that recognize distinct Aβ peptides are commercially available. Examples of such antibodies include anti-β-Amyloid, 1-16 antibody, catalog #803004 and anti-β-Amyloid, 17-24 antibody, catalog #800712, both from BioLegend. According to the manufacturer, the #803004 antibody recognizes an epitope within amino acids 3-8 of beta amyloid (EFRHDS (SEQ ID NO: 39)), while the #800712 antibody recognizes an epitope within amino acids 18-22 of beta amyloid (VFFAE (SEQ ID NO: 40)). The former antibody may bind C-terminally truncated peptides Aβ1-X, where X is between 16 and 42, whereas the latter antibody may bind N-terminally truncated peptides, such as AβX-40 and AβX-42, as well as C-terminally truncated peptides Aβ1-X, where X is between 24 and 42. Certain Aβ peptides may bind to both antibodies, e.g. Aβ1-40 and Aβ1-42.

In an embodiment, the instant specification describes a method for contacting two or more samples, each of which contains at least two distinct peptide analytes, with a corresponding number of bead arrays, each of which contains a reactive site recognizing the peptide analytes, optionally followed by MS detection of the captured analytes from individual reactive sites. The described method is useful for performing epitope mapping assays.

Figure 1C:
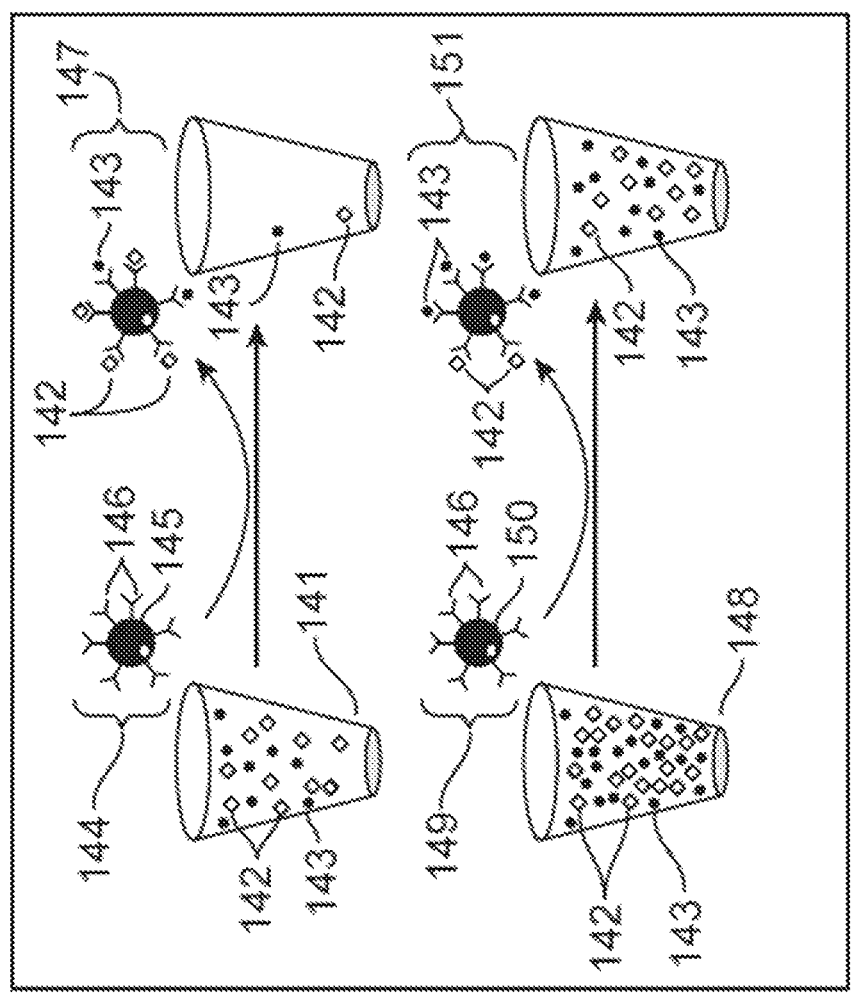

In reference to FIG. 1C, a first sample 141 contains a first peptide 142 and a second peptide 143 that is distinct from the first peptide. A second sample 148 also contains the first peptide and the second peptide. The first sample is brought in contact with a first bead array, which contains a reactive site 144. The reactive site contains a bead 145 and a capture agent 146 that specifically recognizes the first and the second peptides. A binding capacity of the first bead array is greater than the amount of the first and the second peptides in the first sample. The second sample is brought in contact with a second bead array, which contains a reactive site 149. The reactive site contains a bead 150 and the capture agent 146. A binding capacity of the second bead array is lower than the amount of the first and the second peptides in the second sample. Accordingly, the binding capacity of the first bead array is greater than the binding capacity of the second bead array. The two contacting steps occur concurrently, consecutively or partially overlap in time. After the contacting steps, the reacted reactive site 147 of the first bead array and the reacted reactive site 151 of the second bead array are individually analyzed by MS to obtain a ratio of the first peptide to the second peptide in the corresponding reactive site.

In an embodiment, the instant specification describes a method for consecutively contacting a sample that contains at least two distinct target analytes with two or more bead arrays, followed by MS detection of the captured analytes from an individual reactive site of at least one of the bead arrays. The sample is subjected to proteolytic digestion between the two contacting steps. The described method is useful for measuring analytes that have significantly different molecular weights, such as Aβ peptides and protein TAU.

Figure 1D:
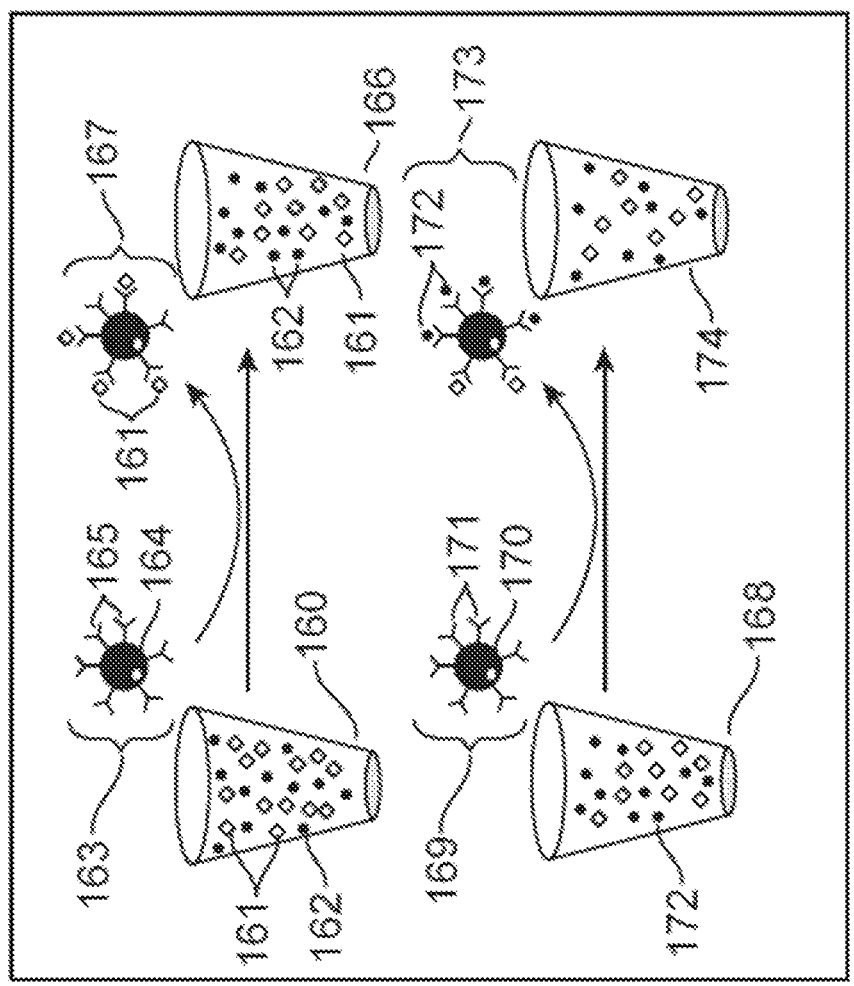

In reference to FIG. 1D, a sample 160 contains a first target 161 and a second target 162 that is distinct from the first target. The sample is brought in contact with a first bead array that contains a reactive site 163. The reactive site contains a bead 164 and a capture agent 165 that specifically recognizes the first target. A binding capacity of the first bead array is greater than, equal to, or lower than the amount of the first target in the sample. After the contacting step, the unreacted portion of the sample 166 now contains reduced amounts of the first target or is depleted of the first target. The unreacted portion of sample 166 is then subjected to enzymatic digestion to produce a digested sample 168 and the digested sample 168 is subsequently brought in contact with a second bead array that contains a reactive site 169. The reactive site contains a bead 170 and a capture agent 171 that specifically recognizes a proteolytic fragment of the second target 172. The second bead array optionally also contains a reactive site that specifically recognizes a proteolytic fragment of the first target. The reacted reactive site 167 of the first bead array and/or the reacted reactive site 173 of the second bead array are then analyzed by mass spectrometry.

The present disclosure is described in the following Examples, which are set forth to aid in the understanding of the disclosure, and should not be construed to limit in any way the scope of the disclosure as defined in the claims which follow thereafter. The following examples are put forth so as to provide those of ordinary skill in the art with a complete disclosure and description of how to make and use the present disclosure, and are not intended to limit the scope of the present disclosure nor are they intended to represent that the experiments below are all or the only experiments performed. Efforts have been made to ensure accuracy with respect to numbers used (e.g. amounts, temperature, volume, time etc.) but some experimental errors and deviations should be accounted for.

EXAMPLES

Materials and Methods

N-Hydroxysuccinimide (NHS)-activated magnetic agarose beads, ITO (Indium Tin Oxide) and gold-coated microscope slides, silicone gaskets and multi-well chambers and methods of making bead arrays are described in the U.S. patent application Ser. No. 16/125,164, publication No. US 2019-0072546 A1.

Unless noted otherwise, consumables such as microcentrifuge tubes, pipette tips, weigh boats etc., were standard research grade. Reagents such as organic solvents, acids, salts, buffers, detergents, MALDI matrices etc., were standard research grade with a purity of 99% or higher and used as received from the manufacturer without further purification. Standard lab equipment included a microcentrifuge, a microplate centrifuge, magnetic tube racks, microtiter plate shaker, vortexer, etc.

Programmable robotic liquid sprayer iMatrixSpray that is capable of dispensing MALDI matrix solutions was from Tardo GmbH (Subingen, Switzerland).

Matrix Assisted Laser Desorption Ionization Time of Flight (MALDI TOF) MS data was acquired on Bruker Daltonics (Billerica MA) Autoflex Speed MALDI TOF-TOF mass spectrometer using FlexControl v.3.4 software and low mass range data acquisition methods supplied by the manufacturer. Unless otherwise indicated, mass spectra were acquired in the positive linear mode, 600-7000 m/z mass range using the laser repetition rate of 2 kHz. Between 2000 and 10000 single shot spectra were collected from individual microarray spots using the random walk method. The instrument laser power was 50%, laser attenuator offset 30%, attenuator range 20%. The voltage settings were 19.50 kV (ion source 1), 18.35 kV (ion source 2) and 6.0 kV (lens). The pulsed ion extraction was 130 ns. The detector gain voltage was 4.0x or 2910 V.

In the positive reflector mode, the spectra were measured in the 900-5000 m/z mass range using the laser repetition rate of 2 kHz. The voltage settings were 19.00 kV (ion source 1), 16.55 kV (ion source 2), 8.45 kV (lens), 21.00 kV (reflector), 9.65 kV (reflector 2). The pulsed ion extraction was 100 ns. The detector gain voltage was 8.1x or 1919 V. The digitizer sampling rate was 4.00 GS/s.

In the MS-MS mode, the spectra were collected using the LIFT method provided by the manufacturer at the laser repetition rate of 2 kHz (parent ions) and 200 Hz (fragment ions). The voltage settings were 6.00 kV (ion source 1), 5.30 kV (ion source 2), 3.00 kV (lens), 27.20 kV (reflector), 11.70 kV (reflector 2), 19.00 kV (lift 1), 4.20 kV (lift 2). The pulsed ion extraction was 100 ns. The reflector gain voltage was 19.4x or 2051 V. The digitizer sampling rate was 2.00 GS/s.

The instrument was externally calibrated in cubic enhanced mode using a mixture of peptides derived from trypsin-digested CAM-modified bovine serum albumin (BSA) supplemented with human insulin and ubiquitin. Molecular weights of the calibration peptides spanned a range between 600 and 8000 Da.

Prior to MS data acquisition, analyte-containing spots within each microarray were identified by visual inspection and their coordinates submitted to AutoXecute module of FlexControl. The analyte-containing spots were identified based on their characteristic appearance due to presence of inner areas devoid of the MALDI matrix that coincide with locations of beads on the microarray slide. MS data was subsequently acquired from the selected spots in automatic mode. Mass spectra collected from each spot were averaged and the averaged spectra from each spot were individually saved.

Mass spectra were processed and analyzed using FlexAnalysis v. 3.4 software. Peaks were detected that had a signal-to-noise ratio of at least 3. In some cases, baseline subtraction procedure was applied to individual mass spectra.

Figure 5A:
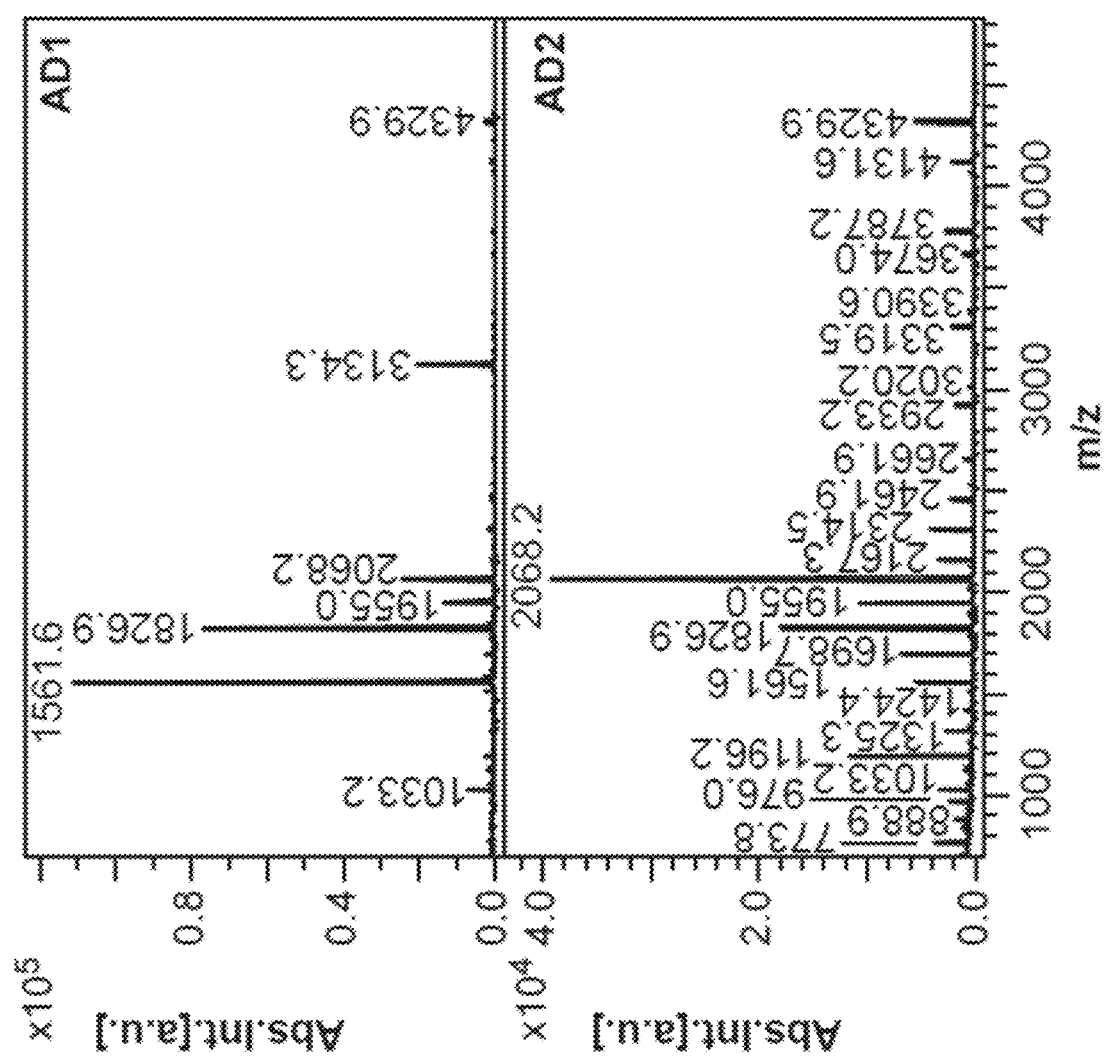
FIG. 5A shows MALDI TOF mass spectra of IP fractions of Aβ peptides obtained from individual CSF samples from human subjects diagnosed with AD.

Unless otherwise indicated, peaks in the mass spectra are labeled using values corresponding to M+, rather than MH+. Unless otherwise indicated, the peak labels are average and not monoisotopic values. For each peak that is assigned to a specific peptide, the signal was detected within 0.3 m/z units from a theoretical mass of that peptide. For example, the peak labeled 4329.8 in FIG. 2 and 4329.9 in FIG. 5A is assigned to Aβ1-40 that has an average molecular weight of 4329.86 and an MH+ value of 4330.89.

Peptide sequencing data was produced using the LIFT method and analyzed using the online program MS-Tag (ProteinProspector, University of California San Francisco). The MS-Tag settings were as follows: database: SwissProt 2017.11.01; taxonomy: *Homo Sapiens*; digest: no enzyme; constant mods: none; variable mods: oxidation (M); parent ion tolerance: 200 ppm; fragment tolerance: 0.8 Da; max mods: 1; instrument: MALDI-TOFTOF.

Experimental Results

Some of the experiments performed using the compositions and methods disclosed in this application and the resulting experimental data are described below.

Example 1

Microarray Reactive Site Configured for Capturing Multiple Aβ Peptides

Purified anti-β-Amyloid, 1-16 antibody was purchased from BioLegend (San Diego CA). The product catalog number is 803004, lot number B259913. According to the manufacturer's application notes, the #803004 antibody "is reactive to amino acid residue 1-16 of beta amyloid. The epitope lies within amino acids 3-8 of beta amyloid (EFRHDS (SEQ ID NO: 39))". The antibody was supplied in BSA-free and azide-free form. After receiving the antibody stock, its concentration was adjusted to 1 mg/ml by diluting with 1×PBS. Approximately 7 μg of the antibody solution was used for direct conjugation to 100 of Protein A+G activated magnetic agarose beads. Individual beads were in the 375 to 400 μm diameter range. The beads containing the antibody were subsequently cross-linked using the previously published procedure utilizing dimethyl pimelimidate dihydrochloride (DMP). An amount of antibody per single bead was estimated to be between 800 and 1000 fmol.

The beads were subsequently transferred into 1× PBS supplemented with 0.03% sodium azide and stored at 4° C. until ready to use.

Example 2

Capturing Multiple Aβ Peptides on a Reactive Site of a Bead Array

Pooled and individual CSF samples were obtained from a US-based commercial biospecimen repository (Proteo-Genex, Inglewood, CA). The CSF samples were from patients diagnosed with Alzheimer's disease (AD) and from age-matching subjects that did not have AD diagnosis (non-AD controls). All samples were obtained using the standard lumbar puncture (spinal tap) procedure, stored at −80° C. and were not subjected to more than 1 freeze-thaw cycle. Immediately before incubation, the samples were thawed on ice.

A 150 μL aliquot of a CSF sample (either pooled or individual) was mixed with 100 μL binding buffer (1× PBS pH 7.4, 2 M KCl) and the solution transferred into a single well of an EPPENDORF® 96 well plate. The well was sealed using PARAFILM® tape to prevent solvent evaporation. A total of 3 microbeads conjugated to #803004 antibody were added to the solution. The IP reaction was carried out by inserting the 96 well plate into the EPPENDORF® Thermomixer C and incubating the microbeads with the solution overnight (12-14 hours) at 4° C. and shaking at 1200 RPM.

The microbeads were subsequently washed to remove non-specifically bound compounds and captured amyloid beta peptides eluted from individual microbeads. The wash and elution procedures are described in the U.S. patent application Ser. No. 16/125,164, publication No. US 2019-0072546 A1. The eluted peptides mixed with CHCA MALDI matrix formed an array containing 500 μm diameter spots. Individual analyte-containing spots were subsequently measured by MALDI TOF MS. The procedure for measuring an array of microspots by MALDI TOF MS is also described in the US 2019-0072546 A1 application.

Example 3

MALDI TOF MS Analysis of Pooled Control and AD CSF Samples

Figure 2:
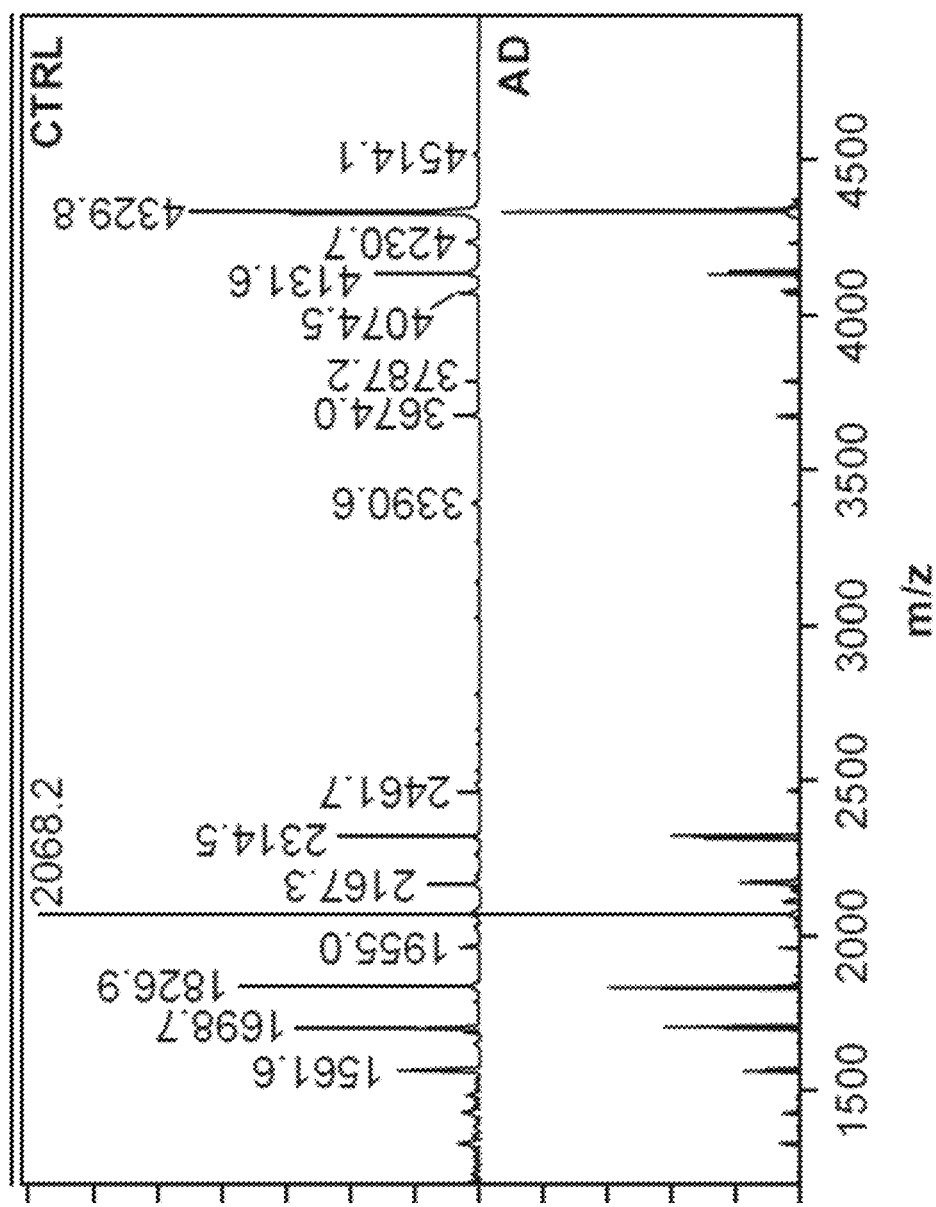
FIG. 2 shows MALDI TOF mass spectra of immunoprecipitated (IP) fractions of Aβ peptides obtained from a pooled CSF sample of Alzheimer's disease (AD) patients and from an age-matching control sample.

FIG. 2 shows mass spectra of pooled non-AD control CSF sample (top trace, labeled CTRL) and pooled AD CSF sample (bottom trace, labeled AD). The two spectra contain multiple peaks that are assigned to various endogenous Aβ peptides of human origin that are present in CSF. The relative intensity of individual peaks closely matches in the two spectra with a few exceptions, as detailed below. For example, intensity ratios for 1561.6/1698.7, 1698.7/1826.9 and 4131.6/4329.8 pairs of peaks are consistently reproducible with less than 10% deviation between the AD and non-AD samples. Moreover, the spectra resemble the previously published MALDI TOF MS spectra of Aβ peptides found in CSF. The data confirms that the experimental conditions for obtaining mass spectra of Aβ peptides from CSF samples are highly reproducible, including (1) reproducible IP of Aβ peptides on individual reactive sites of a bead array using an antibody that recognizes an epitope containing amino acids EFRHDS (SEQ ID NO: 39), (2) reproducible elution of captured Aβ peptides from the bead array and (3) reproducible acquisition of MS data from the eluted Aβ peptides.

The peaks shown in FIG. 2 are assigned to endogenous human CSF Aβ peptides based on MS-MS sequencing. The peak assignments are as follows: 1561.6-Aβ1-13, 1698.7-Aβ1-14, 1826.9-Aβ1-15, 1955.0-Aβ1-16, 2068.2-Aβ1-17, 2167.2-Aβ1-18, 2314.5-Aβ1-19, 2461.7-Aβ1-20, 3390.6-Aβ1-29, 3674.0-Aβ1-33, 3787.2-Aβ1-34, 4074.5-Aβ1-37, 4131.6-Aβ1-38, 4230.7-Aβ1-39, 4329.8-Aβ1-40, 4514.1-Aβ1-42.

Figure 3A:
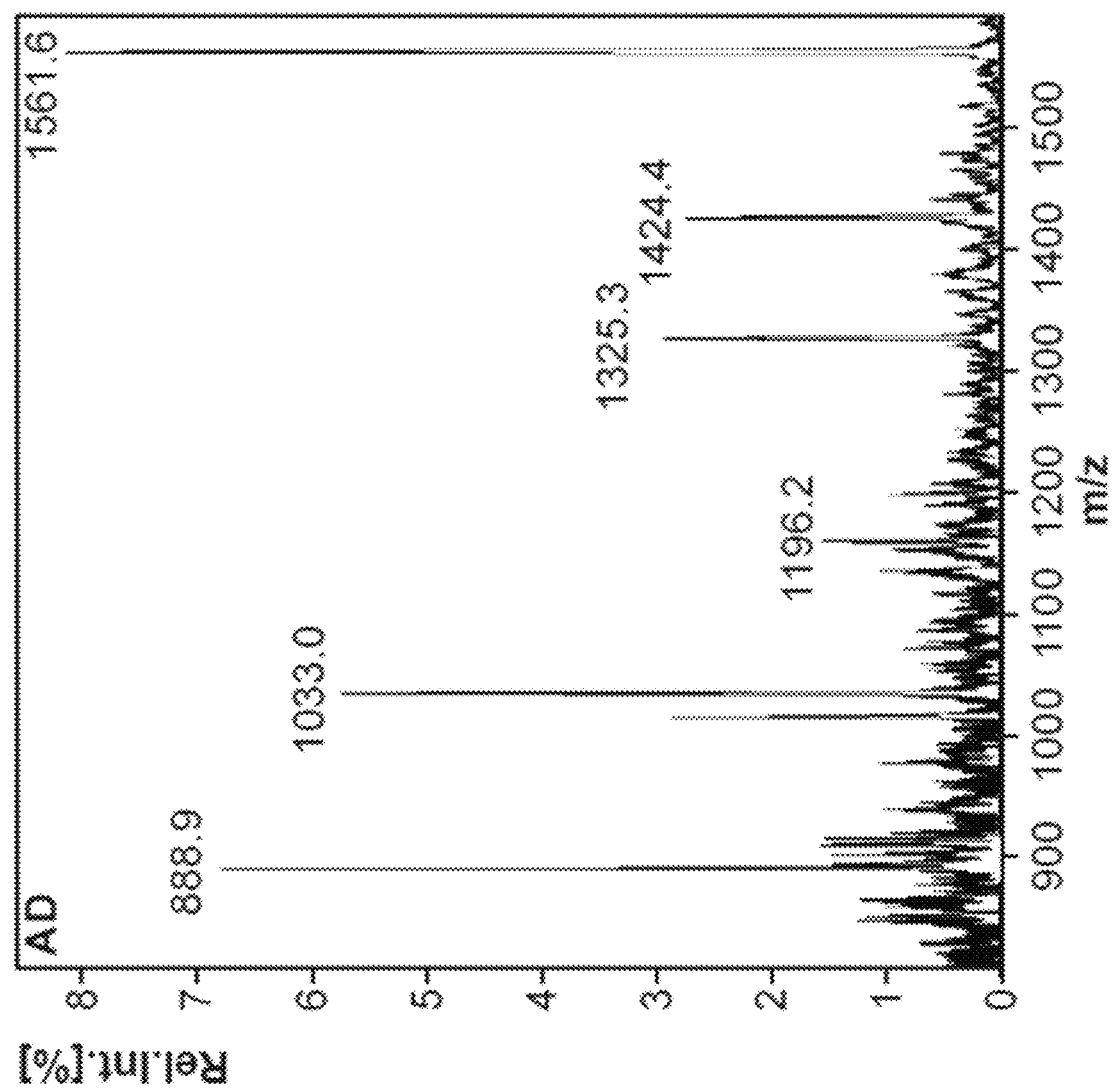
FIG. 3A is an expanded view of the mass spectrum shown in FIG. 2 in the 850-1600 m/z region.

In addition to the strong to medium intensity peaks listed above, the mass spectra also contain multiple lower intensity peaks that are assigned to endogenous human CSF Aβ peptides based on predicted molecular weights. FIG. 3A shows an expanded view of the AD mass spectrum in the 850-1600 m/z region. Peaks detected in this mass range are assigned as follows: 888.9-Aβ1-7, 1033.0-Aβ1-9, 1196.2-Aβ1-10, 1325.3-Aβ1-11, 1424.4-Aβ1-12, 1561.6-Aβ1-13. Intensities of these peaks relative to the intensity of the 2068.2 peak are from about 1.5% (1196.2, Aβ1-10) to about 7% (888.9, Aβ1-7).

Figure 3B:
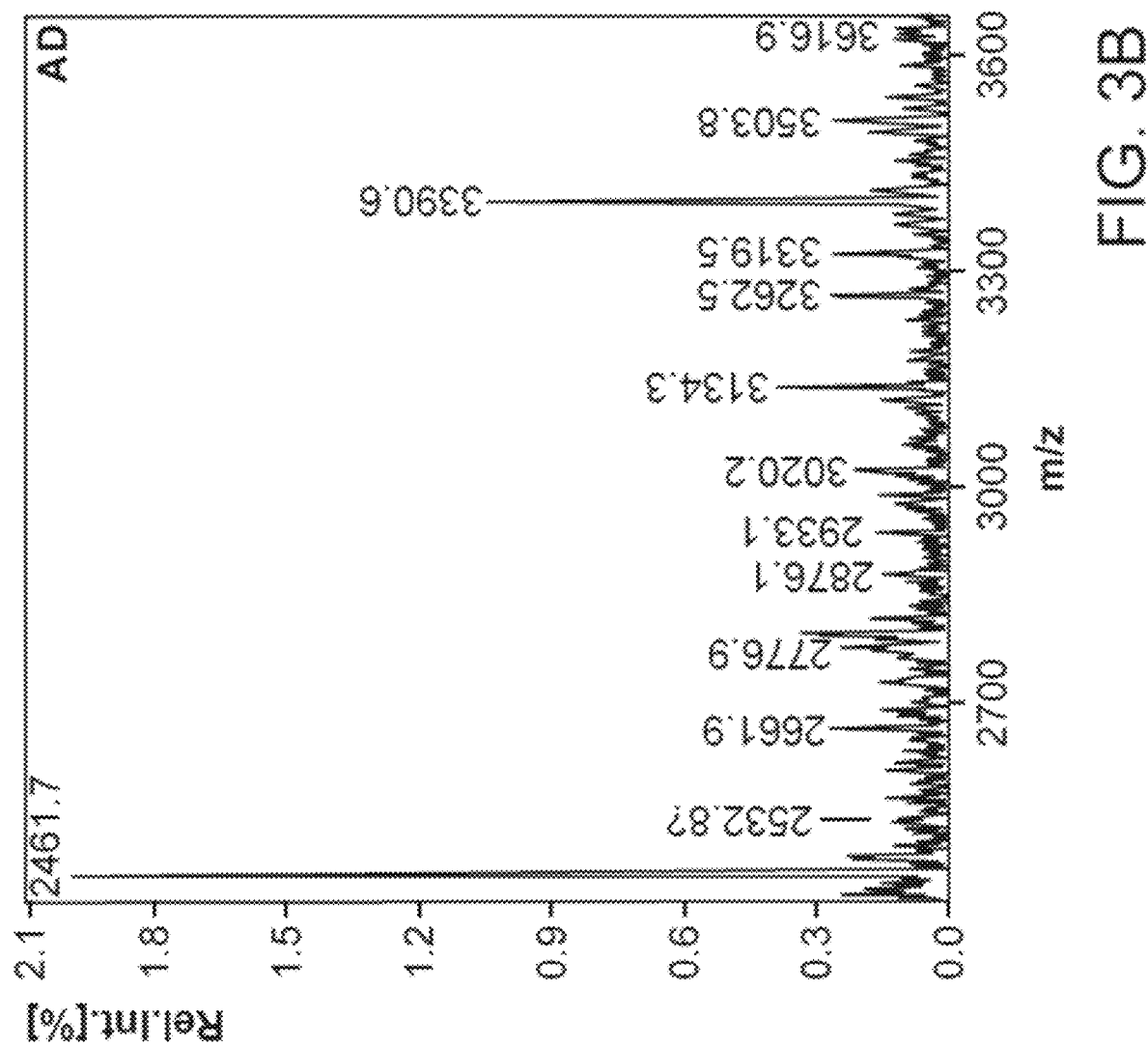
FIG. 3B is an expanded view of the mass spectrum shown in FIG. 2 in the 2400-3650 m/z region.

FIG. 3B shows an expanded view of the AD mass spectrum in the 2400-3650 m/z region. Peaks detected in this mass range are assigned to endogenous human Aβ peptides in CSF as follows: 2461.7-Aβ1-20, 2661.9-Aβ1-22, 2776.9-Aβ1-23, 2876.1-Aβ1-24, 2933.1-Aβ1-25, 3020.2-Aβ1-26, 3134.3-Aβ1-27, 3262.5-Aβ1-28, 3319.5-Aβ1-29, 3390.6-Aβ1-30, 3503.8-Aβ1-31, 3616.9-Aβ1-32. A possible weak peak near 2532.8 may be assigned to Aβ1-21. Intensities of the peaks in this region relative to the intensity of the 2068.2 peak are from about 0.2% (Aβ1-24, Aβ1-25, Aβ1-26) to about 1% (Aβ1-30). All peaks are detectable in both pooled AD and control non-AD spectra.

FIG. 3C shows an expanded view of the control and AD mass spectra in the 3750-4100 m/z region. The spectra are superimposed and normalized to intensity of the 4329.8 (Aβ1-40) peak. Peaks detected in this mass range are assigned to endogenous human CSF Aβ peptides as follows: 3787.2-Aβ1-34, 3918.4-Aβ1-35, 4017.5-Aβ1-36, 4074.5-Aβ1-37. Intensities of the peaks in this region relative to the intensity of the 4329.8 peak are from about 0.3% (Aβ1-35, Aβ1-36) to about 5% (Aβ1-37). Normalizing the Aβ1-40 peak also normalizes the Aβ1-36 and Aβ1-37 peaks, while the Aβ1-34 peak is about 30% more intense in the AD sample.

Figure 3D:
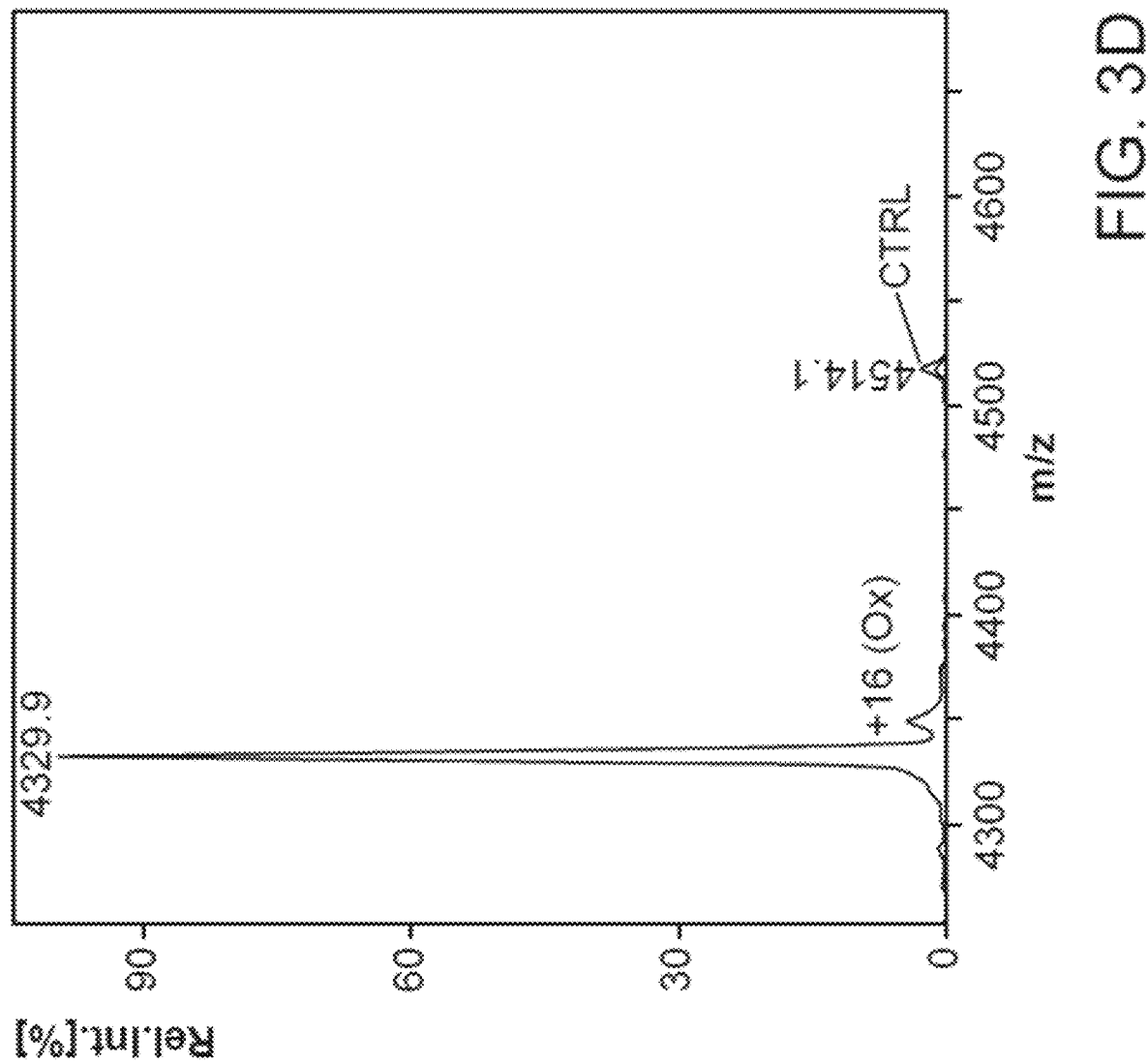
FIG. 3D is an expanded view of the mass spectra shown in FIG. 2 in the 4300-4700 m/z region.

FIG. 3D shows an expanded view of the control and AD mass spectra in the 4300-4700 m/z region. Again, the spectra are superimposed and normalized to the Aβ1-40 peak. Peaks detected in this mass range include 4514.1 that is assigned to Aβ1-42. The relative intensity of Aβ1-42 peak is higher in the non-AD control sample. Another peak in this region is 4345.9, which has similar intensity in both mass spectra and is assigned to Aβ1-40 containing oxidized Met35 (Aβ1-40 (ox)). Satellite peaks shifted by +16 m/z units are also detected for smaller fragments containing oxidized Met35, including Aβ1-35 (ox), Aβ1-36 (ox), Aβ1-37 (ox), 1-38 (ox) and Aβ1-39 (ox).

Figure 3E:
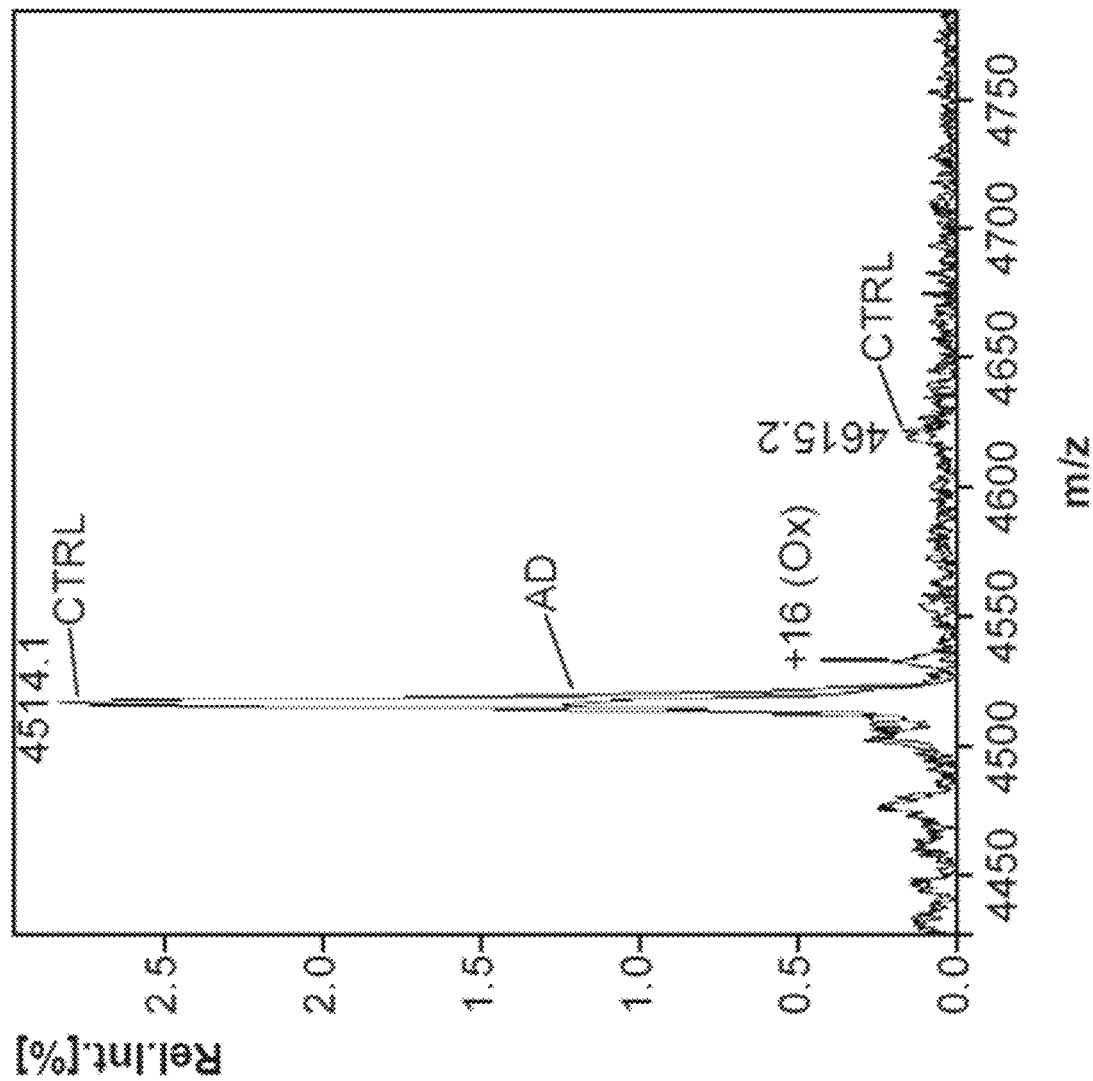
FIG. 3E is an expanded view of the mass spectra shown in FIG. 2 in the 4450-4750 m/z region.

FIG. 3E shows an expanded view of the control and AD mass spectra in the 4450-4750 m/z region. The spectra are superimposed and normalized to the Aβ1-40 peak. The Aβ1-42 peak at 4514.1 has about 2.5-fold greater intensity in the non-AD control. A +16 m/z shifted peak is also detected and assigned to Aβ1-42 (ox), that is Aβ1-42 peptide containing oxidized Met35. Therefore, the spectra allow comparison of abundance of Aβ1-42 (ox) peptides between AD and non-AD CSF samples. A peak is also detected at 4615.2 that corresponds to Aβ1-43. The Aβ1-43 peak is stronger in the non-AD control.

Example 4

Figure 4:
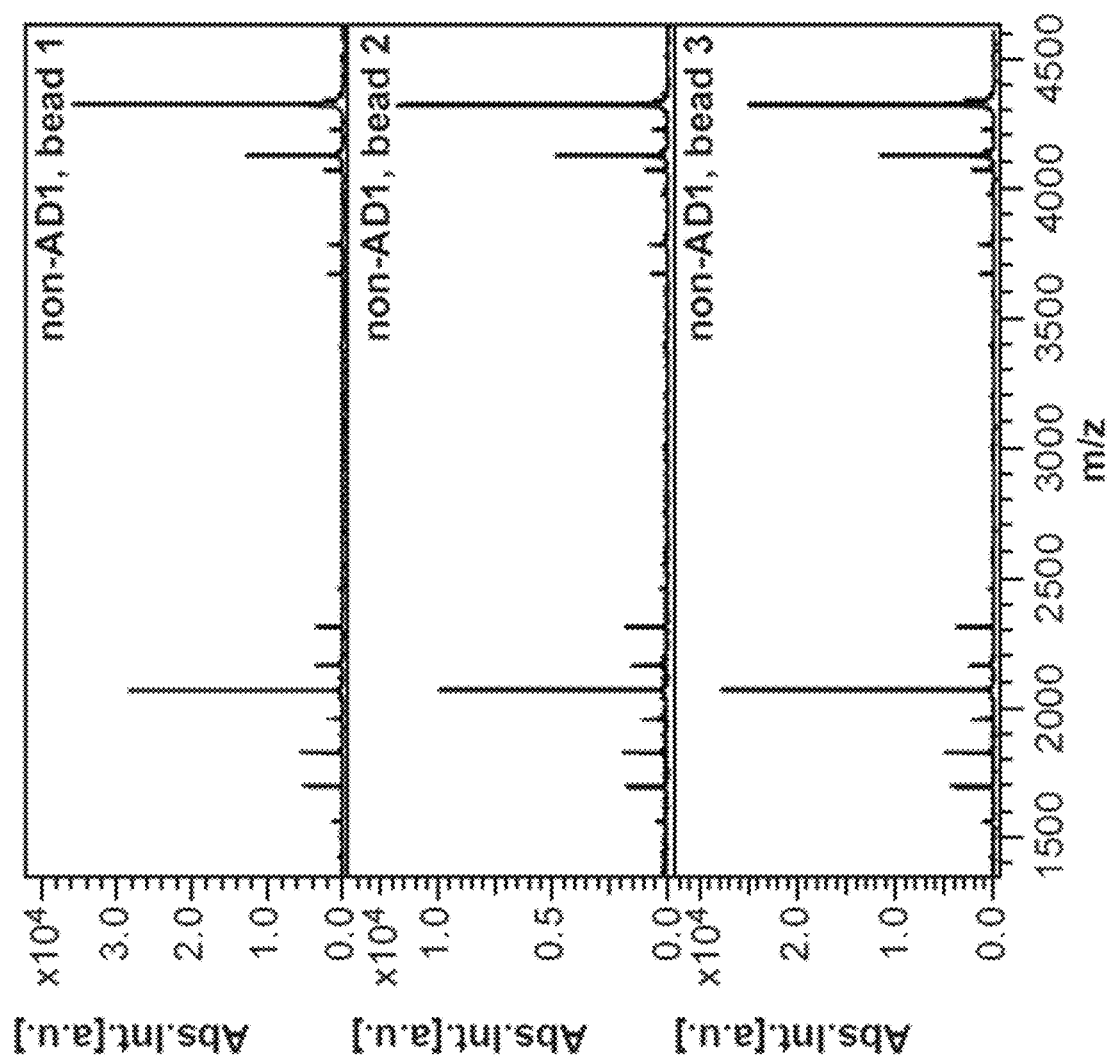
FIG. 4 shows MALDI TOF mass spectra of IP fractions of Aβ peptides obtained from replicate reactive sites of a bead array.

Reproducible Aβ Peptide IP Enrichment on Multiple Reactive Sites of a Bead Array FIG. 4 shows 3 mass spectra that are independently measured from 3 distinct reactive sites of a bead array. The sample is 150 μL of non-pooled CSF obtained from a human subject that was not diagnosed with AD. The pattern of peaks and their relative intensity are highly reproducible across all spectra, particularly for peaks of similar m/z values, e.g. peaks within the 1,500-2,000 region and within the 4,000-4,500 m/z region.

Example 5

Different Aβ Profiles of Individual CSF Samples

FIG. 5A shows representative mass spectra that are measured from non-pooled CSF samples from different human subjects that were not diagnosed with AD. The two spectra show dramatically different patterns with a significantly lower number of peaks detected in sample AD1 compared to sample AD2. In particular, strong peaks are detected in the latter sample at 2661.9 (Aβ1-22) and 2933.1 (Aβ1-25) that were weak in the pooled AD CSF sample.

Figure 5B:
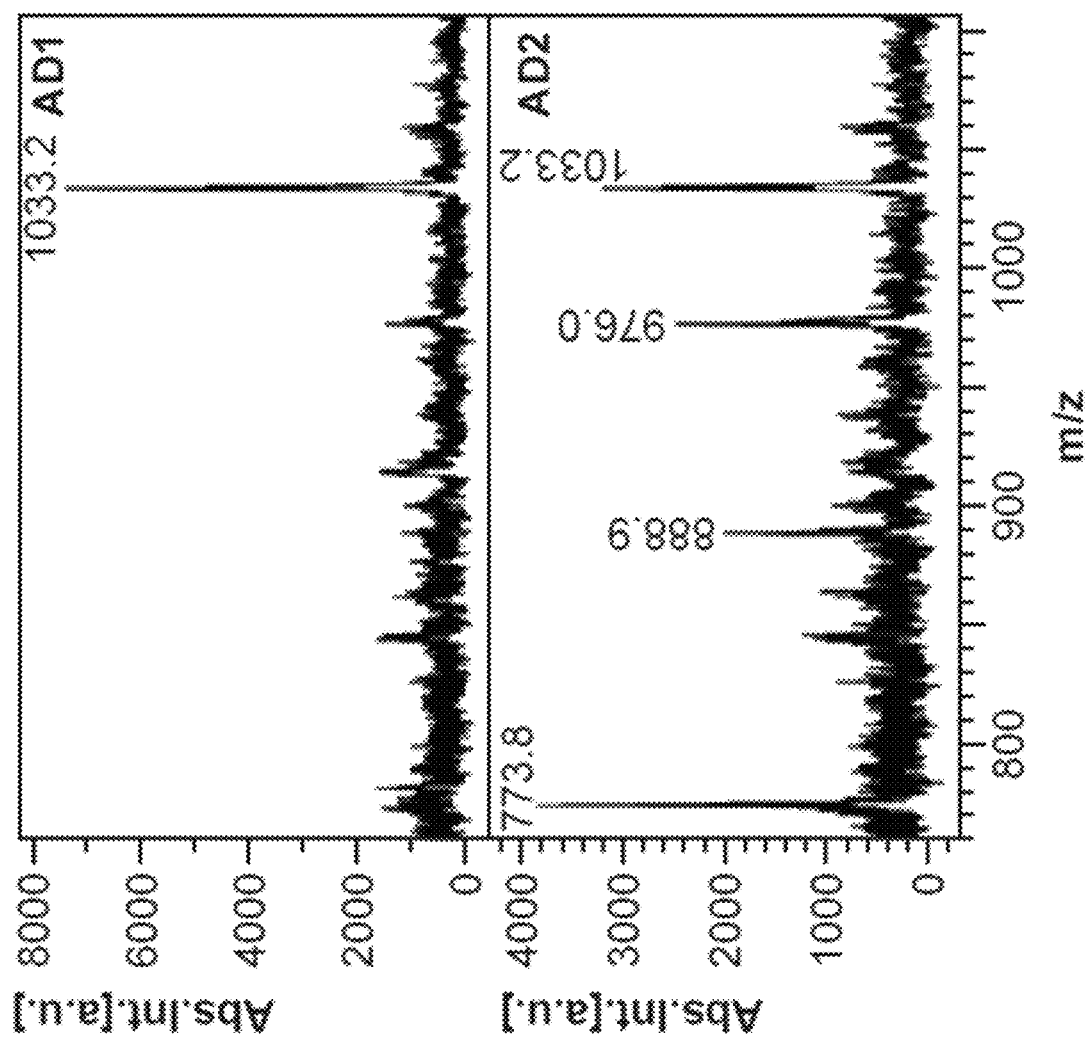
FIG. 5B is an expanded view of the mass spectra shown in FIG. 5A in the 750-1100 m/z region.

FIG. 5B shows an expanded view of the AD1 and AD2 mass spectra in the 750-1100 m/z region. The AD2 spectrum contains peaks at 773.8 (Aβ1-6), 888.9 (Aβ1-7) and 976.0

(Aβ1-8) that are either not detected or very weak in the AD1 spectrum. Both spectra contain a peak at 1033.2 (Aβ1-9).

Figure 6:
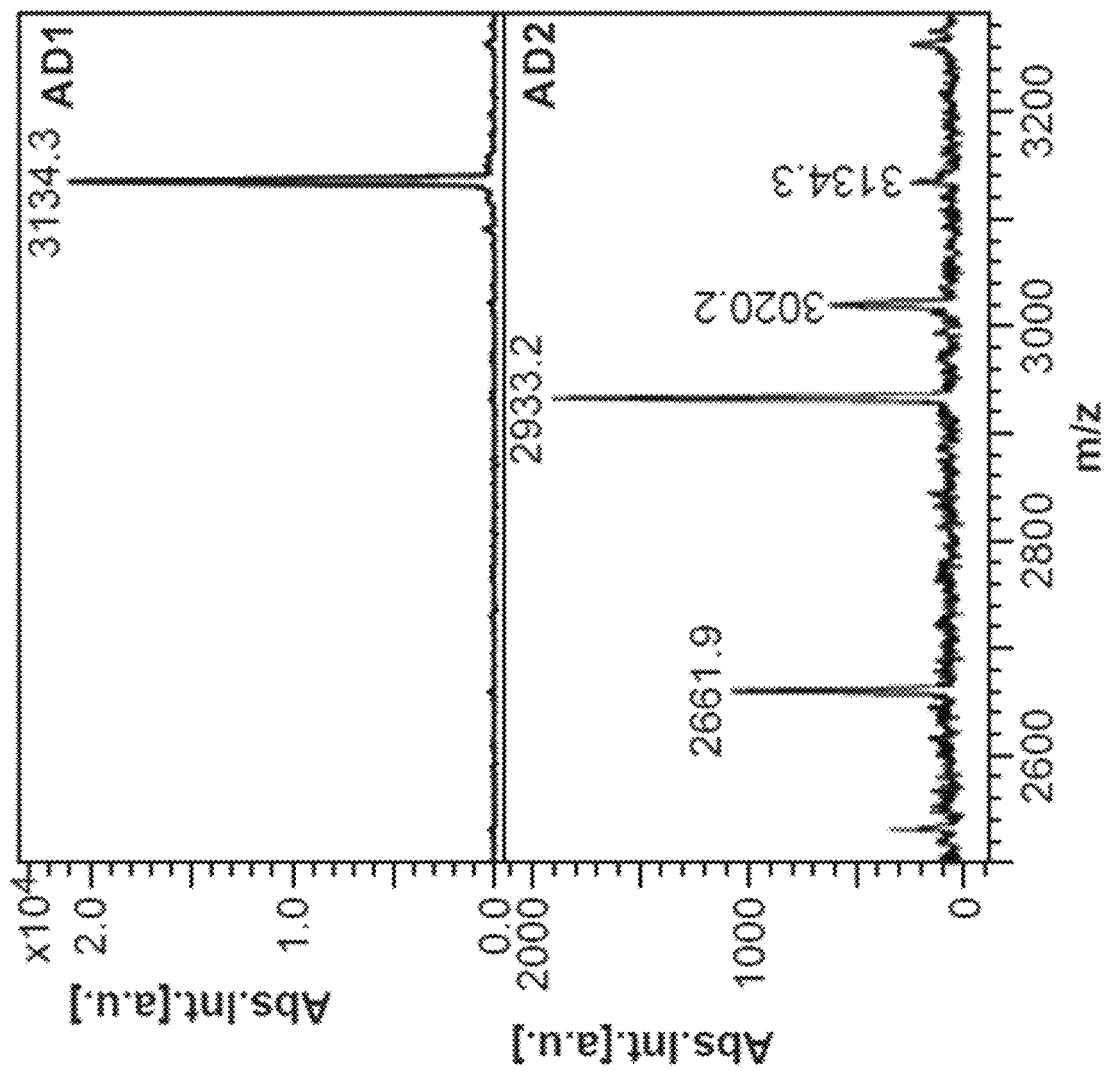
FIG. 6 is an expanded view of the mass spectra shown in FIG. 5A in the 2600-3200 m/z region.

FIG. 6 shows an expanded view of the AD1 and AD2 mass spectra in the 2600-3200 m/z region. The AD2 spectrum contains peaks at 2661.9 (Aβ1-22), 2933.2 (Aβ1-25) and 3020.2 (Aβ1-26) that are not detected in the AD1 spectrum. By contrast, the 3134.3 peak (Aβ1-27) is stronger in the AD1 spectrum.

Example 6

Different Aβ Peptide Abundance Patterns in Individual CSF Samples

Figure 7:
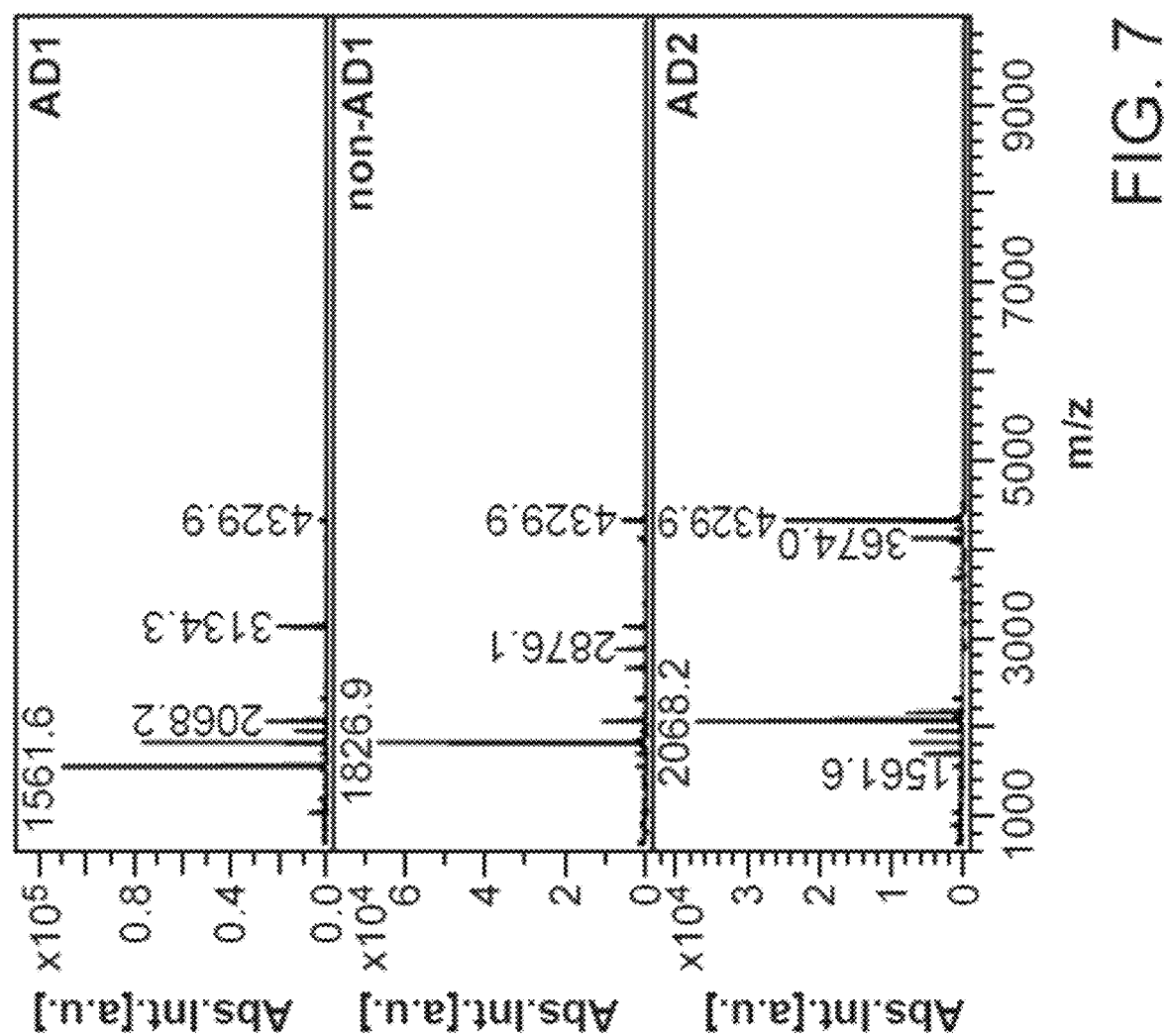
FIG. 7 shows MALDI TOF mass spectra of IP fractions of Aβ peptides obtained from individual CSF samples from selected human subjects.

FIG. 7 shows mass spectra that are measured from 3 individual human subjects, two diagnosed with AD (AD1 and AD2) and one not diagnosed with AD (non-AD1). The volume of CSF from each subject was not greater than 0.25 ml (250 μL).

All spectra contain the Aβ1-40 and Aβ1-42 peptide peaks. The Aβ1-40 to Aβ1-42 peak ratio is consistent with the disease diagnosis, e.g. the intensity of Aβ1-42 peak relative to Aβ1-40 peak is higher in the non-AD1 sample.

By contrast, very different peak patterns are observed in the 1500-3500 m/z region indicating significantly different abundance levels of the corresponding Aβ peptides in their respective samples. Specifically, the 1561.6 (Aβ1-13), 1826.9 (Aβ1-15) and 2068.2 (Aβ1-17) peaks have significantly different intensities in 3 spectra.

In this Example, the samples were classified into 3 different groups according to intensities of signals from peptides Aβ1-11 through Aβ1-27. Detecting signals from such peptides may be useful in classifying human subjects that have a neurological disease other than Alzheimer's.

Example 7

Different Aβ Peptide Abundance Patterns in Individual Non-AD CSF Samples

Figure 8:
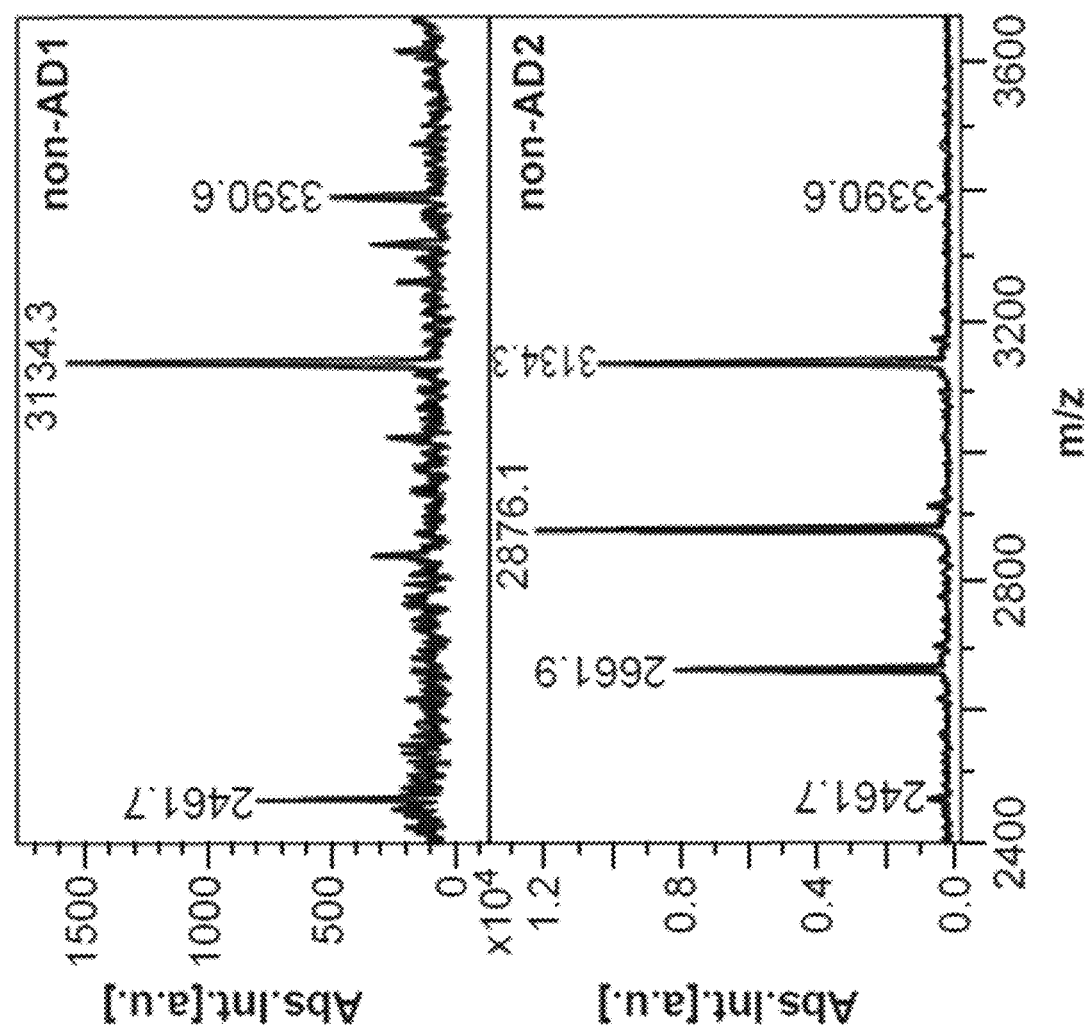
FIG. 8 shows MALDI TOF mass spectra of IP fractions of Aβ peptides obtained from individual CSF samples from selected human subjects.

FIG. 8 shows mass spectra that are measured from 2 individual human subjects that are not diagnosed with AD (non-AD1 and non-AD2). Both the non-AD1 and non-AD2 spectra contain the Aβ1-40 and Aβ1-42 peptide peaks. The Aβ1-40 to Aβ1-42 peak ratio is similar in the two samples, with the coefficient of variation (CV) being less than 10%.

By contrast, very different peak patterns are observed in the 2400-3600 m/z region indicating significantly different abundance levels of the corresponding Aβ peptides in their respective samples. Specifically, the non-AD1 sample contains a medium intensity peak at 3134.3 (Aβ1-27) and weak peaks at 2461.7 (Aβ1-20) and 3390.6 (Aβ1-30) while the non-AD2 sample contains strong peaks at 2661.9 (Aβ1-22), 2876.1 (Aβ1-24) and 3134.4 (Aβ1-27). The latter peaks were detected with the signal-to-noise ratios greater than 100:1.

Therefore, signals from peptides Aβ1-20 (2461.7), Aβ1-22 (2661.9), Aβ1-24 (2876.1) and Aβ1-27 (3134.4) are potentially useful in classifying human subjects that are not diagnosed with AD. Specifically, such signals may be used to assign the subject to a diseased group, the disease being a neurological disease other than AD.

Example 8

Detection of Aβ1-22 and Aβ1-23 Peptides

Figure 9:
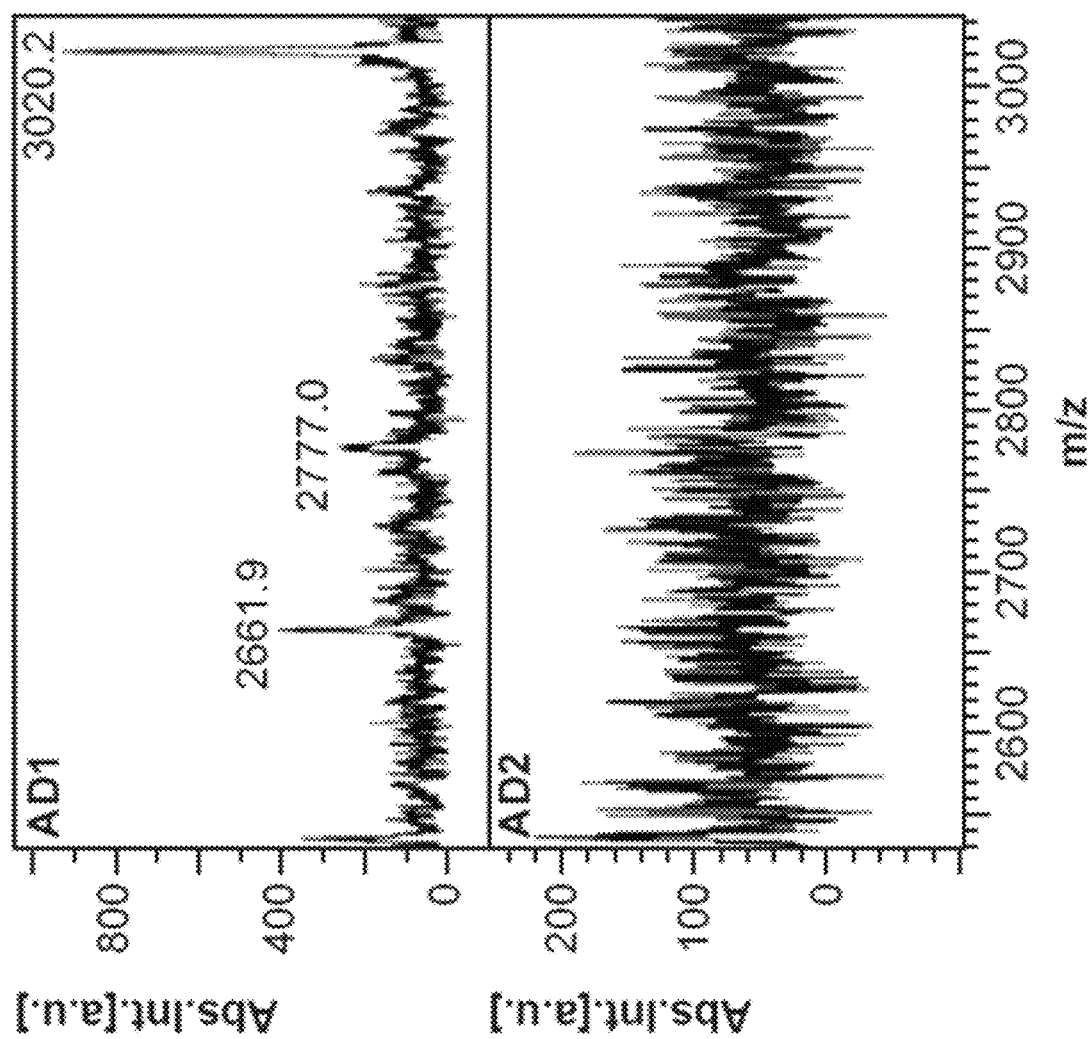
FIG. 9 shows MALDI TOF mass spectra of IP fractions of Aβ peptides obtained from individual CSF samples from selected human subjects diagnosed with AD.

FIG. 9 shows mass spectra that are measured from 2 individual human subjects diagnosed with AD (AD1 and AD2). The AD1 spectrum contains weak peaks at 2661.9 (Aβ1-22), 2777.0 (Aβ1-23) and 3020.2 (Aβ1-26). By contrast the AD2 spectrum does not contain detectable signals from any of these Aβ peptides.

Example 9

Detection of Aβ1-32 Peptide

Figure 10:
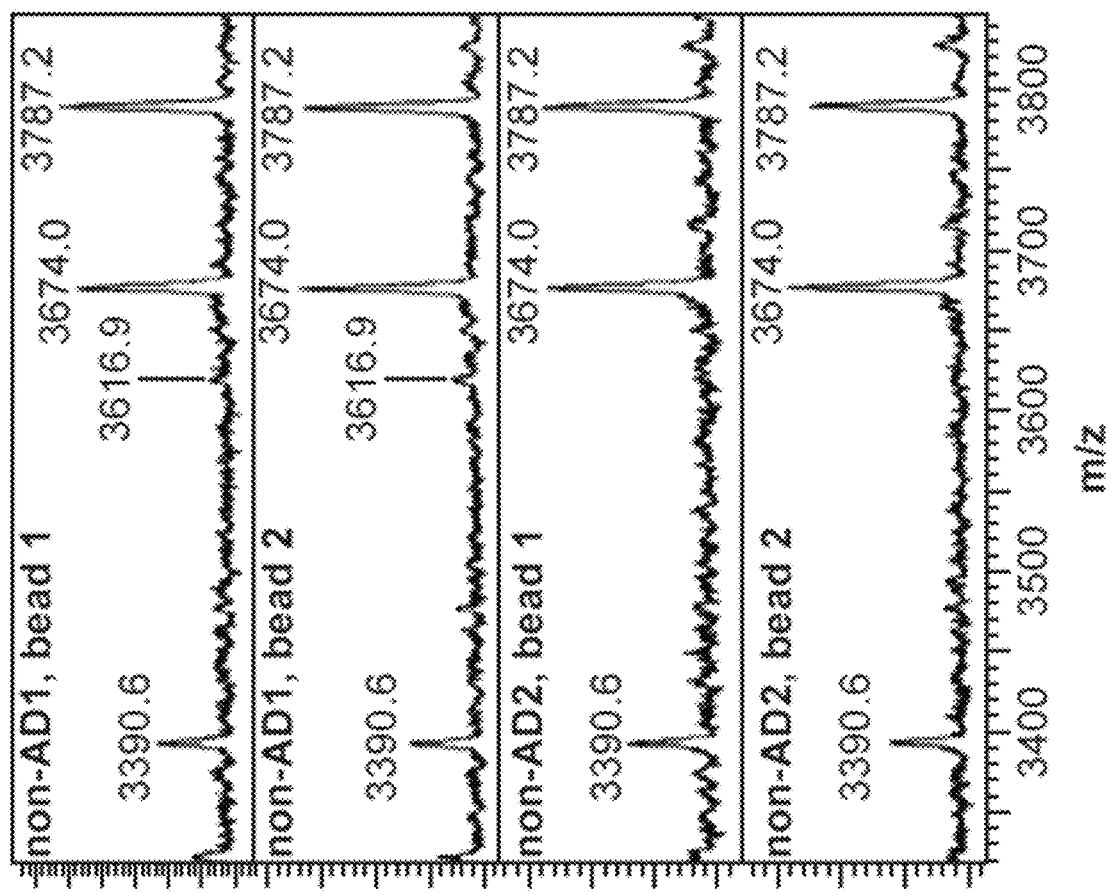
FIG. 10 shows replicate MALDI TOF mass spectra of IP fractions of Aβ peptides obtained from individual CSF samples from selected human subjects.

FIG. 10 shows mass spectra that are measured from replicate reactive sites (bead 1 and bead 2) from 2 individual human subjects that are not diagnosed with AD (non-AD1 and non-AD2). The non-AD1 spectrum contains weak but reproducible peak at 3616.9 (Aβ1-32) and also peaks at 3390.6 (Aβ1-30), 3674.0 (Aβ1-33) and 3787.2 (Aβ1-34). By contrast, the non-AD2 spectrum does not contain the 3616.9 peak but contains the 3390.6, 3674.0 and 3787.2 peaks that have similar relative intensity as the corresponding peaks in the non-AD1 spectrum.

Example 10

Consecutive Enrichment of Aβ Peptides

A CSF sample from a human subject that was not diagnosed with AD was subjected to an IP reaction using the previously described methods. The unreacted portion of the sample (the pass-through) was subsequently frozen and used within several days for a second IP reaction. The conditions of the first and the second IP reactions were identical.

Figure 11:
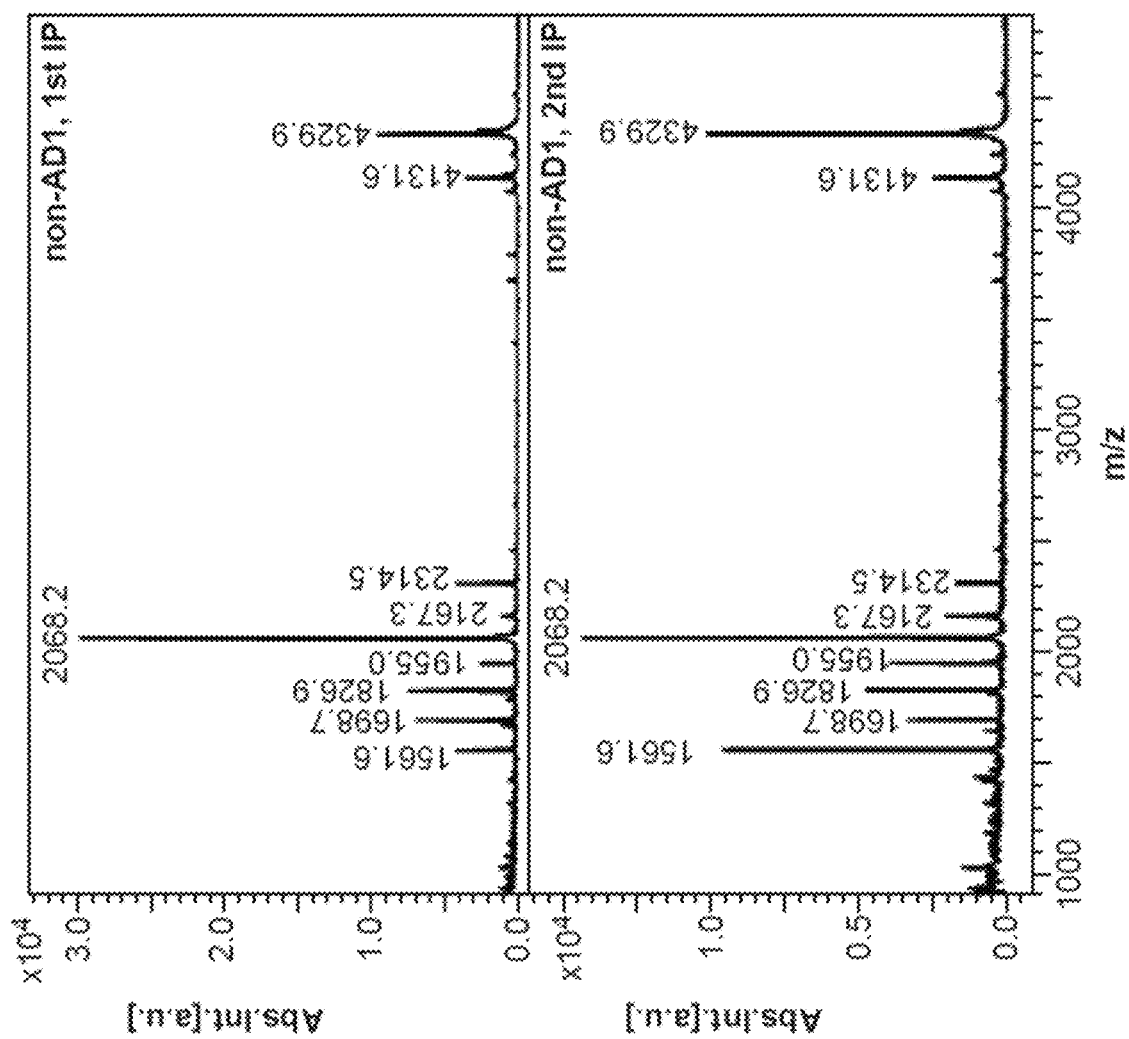
FIG. 11 shows MALDI TOF mass spectra of fractions of Aβ peptides obtained by consecutive IP reactions from an individual CSF sample.

FIG. 11 shows mass spectra that are measured from the first IP reaction (top trace) and the second IP reaction (bottom trace). Overall, the spectra are very similar therefore confirming that the #803004 antibody specifically captures multiple Aβ peptides without a strong preference for a particular peptide or a group of peptides. The data also confirms that the binding capacity of the bead array is lower than a combined amount of the Aβ peptides in the sample. There is an increase in the relative intensity of 1561.6 peak (Aβ1-13) in the second IP reaction. That effect may be attributed to an extra freeze-thaw cycle. Therefore, the signal from Aβ1-13 was used to monitor handling conditions of a CSF sample, such as the number of freeze-thaw cycles.

This Example demonstrates a subsequent IP reaction performed on a sample that was previously subjected to another IP reaction using an antibody that specifically recognizes an endogenous Aβ peptide. While an identical antibody was used in both IP reactions, an alternative scenario is to use distinct antibodies that specifically recognize Aβ peptides, such as the previously described antibodies #803004, #15126 and #8243.

Example 11

Sequence Assignment of Aβ Peptides

Figure 12:
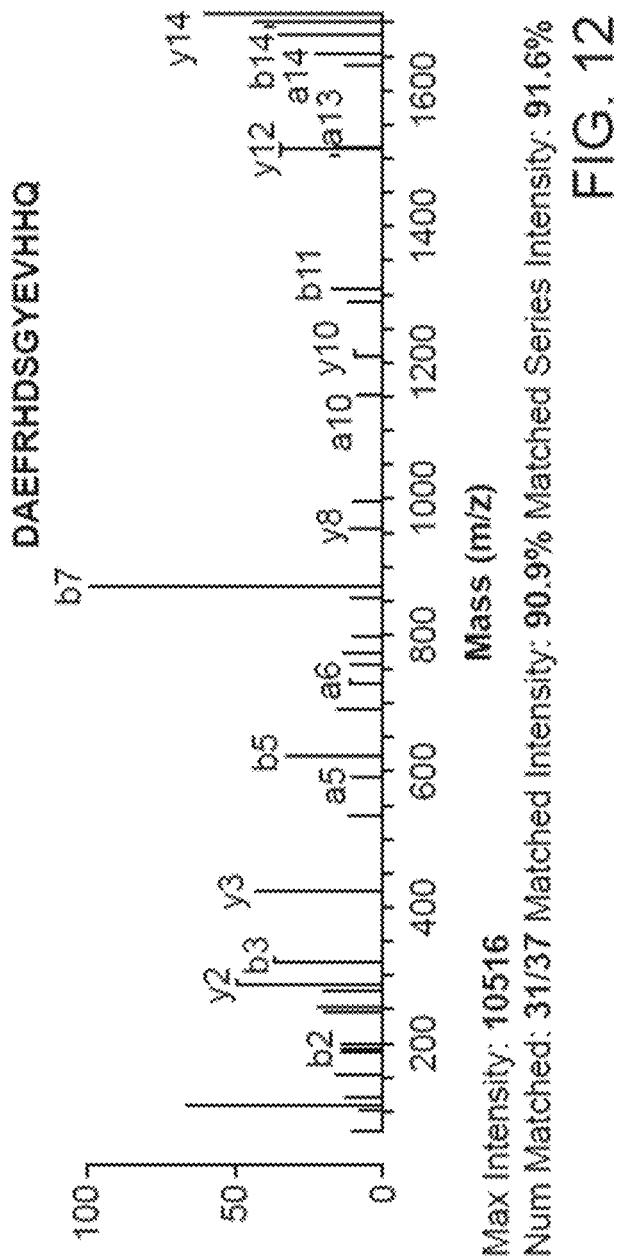
FIG. 12 shows MALDI TOF-TOF MS sequence assignment of the 1826.9 peak to Aβ1-15 peptide (SEQ ID NO: 10).

The majority of peaks shown in FIGS. 2 and 5A were subjected to MS-MS (MS2) sequencing to confirm their identity. The details of MS-MS data acquisition and data analysis protocols are described above. FIG. 12 shows an example of assigning the 1826.9 peak to Aβ1-13 peptide. MS-MS assignments were obtained for other Aβ peptides also.

All patents, patent applications, and published references cited herein are hereby incorporated by reference in their entirety. While the present disclosure has been described in connection with the specific embodiments thereof, it will be understood that it is capable of further modification. Furthermore, this application is intended to cover any variations, uses, or adaptations of the disclosure, including such departures from the present disclosure as come within known or customary practice in the art to which the disclosure pertains, and as fall within the scope of the appended claims.

What is claimed is:

1. A method for analyzing a biological sample, the method comprising the steps of:
   obtaining a plurality of endogenous amyloid beta (Aβ) peptides by subjecting a biological sample containing human cerebrospinal fluid (CSF) to immunoprecipitation (IP), and
   analyzing at least one of the plurality of endogenous Aβ peptides using mass spectrometry,
   wherein the step of analyzing at least one of the plurality of endogenous Aβ peptides using mass spectrometry comprises obtaining a mass spectrometry signal from at least one endogenous CSF Aβ peptide selected from the group of Aβ1-6, Aβ1-7, Aβ1-8, Aβ1-9, Aβ1-10, Aβ1-21, Aβ1-22, Aβ1-23, Aβ1-24, Aβ1-25, Aβ1-26, Aβ1-31, and Aβ1-32.

2. The method of claim 1 wherein the step of analyzing at least one of the plurality of Aβ peptides using mass spectrometry comprises obtaining mass spectrometry signals from at least one endogenous CSF peptide selected from the group of Aβ1-6, Aβ1-7, Aβ1-8, Aβ1-9, and Aβ1-10 and from at least one endogenous CSF peptide selected from the group of Aβ1-21, Aβ1-22, Aβ1-23, Aβ1-24, Aβ1-25, and Aβ1-26.

3. The method of claim 1 wherein the step of analyzing at least one of the plurality of Aβ peptides using mass spectrometry comprises obtaining mass spectrometry signals from at least two endogenous CSF peptides that differ in a single terminal amino acid, the at least two peptides being selected from Aβ1-6, Aβ1-7, Aβ1-8, Aβ1-9, Aβ1-10, Aβ1-21, Aβ1-22, Aβ1-23, Aβ1-24, Aβ1-25, Aβ1-26, Aβ1-31, and Aβ1-32.

4. The method of claim 1 wherein the step of analyzing at least one of the plurality of Aβ peptides using mass spectrometry further comprises the step of additionally obtaining a mass spectrometry signal from at least one endogenous CSF peptide selected from the group of Aβ1-12, Aβ1-13, Aβ1-14, Aβ1-14, Aβ1-29, Aβ1-35, Aβ1-36, and Aβ1-43.

5. The method of claim 1 wherein the step of analyzing at least one of the plurality of Aβ peptides using mass spectrometry further comprises the step of additionally obtaining mass spectrometry signals from at least two of Aβ1-35 (ox), Aβ1-36 (ox), Aβ1-37 (ox), Aβ1-38 (ox), Aβ1-39 (ox), Aβ1-40 (ox), and Aβ1-42 (ox).

6. The method of claim 1 wherein the analyzing step is performed such that the mass spectrometry signal has a signal-to-noise ratio that is greater than 100:1.

7. The method of claim 1 wherein a volume of the human CSF in the biological sample does not exceed 1 milliliter (ml).

8. The method of claim 1 wherein the analyzing step comprises obtaining a mass spectrum from a single reactive site of a bead array.

9. The method of claim 1 further comprising the step of using the signal to assign the biological sample to a diseased group.

10. The method of claim 1 wherein the human CSF is from a human subject that was not diagnosed with a neurological disease.

11. The method of claim 1 wherein the human CSF is from a human subject that has or is suspected of having a neurological disease other than Alzheimer's disease.

12. A method of for analyzing a biological sample, the method comprising the steps of:
    obtaining a plurality of endogenous amyloid beta (Aβ) peptides by subjecting a biological sample containing human cerebrospinal fluid (CSF) to immunoprecipitation (IP), and
    analyzing at least one of the plurality of endogenous AP peptides using mass spectrometry,
    wherein the step of analyzing at least one of the plurality of endogenous Aβ peptides using mass spectrometry comprises obtaining a mass spectrometry signal from at least one endogenous CSF Aβ peptide selected from the group of Aβ1-6, Aβ1-7, Aβ1-8, Aβ1-9, Aβ1-10, Aβ1-11, Aβ1-21, Aβ1-22, Aβ1-23, Aβ1-24, Aβ1-25, Aβ1-26, Aβ1-31, and Aβ1-32, and
    wherein the biological sample was previously subjected to IP using an antibody that specifically recognizes an endogenous Aβ peptide.

13. The method of claim 12 wherein the step of analyzing at least one of the plurality of Aβ peptides using mass spectrometry comprises obtaining mass spectrometry signals from at least one endogenous CSF peptide selected from the group of Aβ1-6, Aβ1-7, Aβ1-8, Aβ1-9, Aβ1-10, and Aβ1-11 and from at least one endogenous CSF peptide selected from the group of Aβ1-21, Aβ1-22, Aβ1-23, Aβ1-24, Aβ1-25, and Aβ1-26.

14. The method of claim 12 wherein the step of analyzing at least one of the plurality of Aβ peptides using mass spectrometry comprises obtaining mass spectrometry signals from at least two endogenous CSF peptides that differ in a single terminal amino acid, the at least two peptides being selected from Aβ1-6, Aβ1-7, Aβ1-8, Aβ1-9, Aβ1-10, Aβ1-11, Aβ1-21, Aβ1-22, Aβ1-23, Aβ1-24, Aβ1-25, Aβ1-26, Aβ1-31, and Aβ1-32.

15. A method for analyzing a biological sample, the method comprising the steps of:
    obtaining a first plurality of endogenous amyloid beta (Aβ) peptides by subjecting a biological sample containing human cerebrospinal fluid (CSF) to immunoprecipitation (IP) using a first antibody,
    then obtaining a second plurality of endogenous Aβ peptides by subjecting the biological sample to IP using a second antibody, and analyzing at least one of the first and the second pluralities using mass spectrometry, wherein the analyzing step comprises obtaining a mass spectrometry signal from at least one endogenous CSF Aβ peptide selected from the group of Aβ1-6, Aβ1-7, Aβ1-8, Aβ1-9, Aβ1-10, Aβ1-11, Aβ1-21, Aβ1-22, Aβ1-23, Aβ1-24, Aβ1-25, Aβ1-26, Aβ1-31, and Aβ1-32.

16. The method of claim 15 wherein the step of analyzing at least one of the plurality of Aβ peptides using mass spectrometry comprises obtaining mass spectrometry signals from at least one endogenous CSF peptide selected from the group of Aβ1-6, Aβ1-7, Aβ1-8, Aβ1-9, Aβ1-10, and Aβ1-11 and from at least one endogenous CSF peptide selected from the group of Aβ1-21, Aβ1-22, Aβ1-23, Aβ1-24, Aβ1-25, and Aβ1-26.

17. The method of claim 15 wherein the step of analyzing at least one of the plurality of Aβ peptides using mass spectrometry comprises obtaining mass spectrometry signals from at least two endogenous CSF peptides that differ in a single terminal amino acid, the at least two peptides being selected from Aβ1-6, Aβ1-7, Aβ1-8, Aβ1-9, Aβ1-10, Aβ1-11, Aβ1-21, Aβ1-22, Aβ1-23, Aβ1-24, Aβ1-25, Aβ1-26, Aβ1-31, and Aβ1-32.

\* \* \* \* \*

```
                              SEQUENCE LISTING

<160> NUMBER OF SEQ ID NOS: 40

<210> SEQ ID NO 1
<211> LENGTH: 6
<212> TYPE: PRT
<213> ORGANISM: Homo sapiens

<400> SEQUENCE: 1

Asp Ala Glu Phe Arg His
1               5

<210> SEQ ID NO 2
<211> LENGTH: 7
<212> TYPE: PRT
<213> ORGANISM: Homo sapiens

<400> SEQUENCE: 2

Asp Ala Glu Phe Arg His Asp
1               5

<210> SEQ ID NO 3
<211> LENGTH: 8
<212> TYPE: PRT
<213> ORGANISM: Homo sapiens

<400> SEQUENCE: 3

Asp Ala Glu Phe Arg His Asp Ser
1               5

<210> SEQ ID NO 4
<211> LENGTH: 9
<212> TYPE: PRT
<213> ORGANISM: Homo sapiens

<400> SEQUENCE: 4

Asp Ala Glu Phe Arg His Asp Ser Gly
1               5

<210> SEQ ID NO 5
<211> LENGTH: 10
<212> TYPE: PRT
<213> ORGANISM: Homo sapiens

<400> SEQUENCE: 5

Asp Ala Glu Phe Arg His Asp Ser Gly Tyr
1               5                   10

<210> SEQ ID NO 6
<211> LENGTH: 11
<212> TYPE: PRT
<213> ORGANISM: Homo sapiens

<400> SEQUENCE: 6

Asp Ala Glu Phe Arg His Asp Ser Gly Tyr Glu
1               5                   10

<210> SEQ ID NO 7
<211> LENGTH: 12
<212> TYPE: PRT
<213> ORGANISM: Homo sapiens
```

<400> SEQUENCE: 7

Asp Ala Glu Phe Arg His Asp Ser Gly Tyr Glu Val
1               5                   10

<210> SEQ ID NO 8
<211> LENGTH: 13
<212> TYPE: PRT
<213> ORGANISM: Homo sapiens

<400> SEQUENCE: 8

Asp Ala Glu Phe Arg His Asp Ser Gly Tyr Glu Val His
1               5                   10

<210> SEQ ID NO 9
<211> LENGTH: 14
<212> TYPE: PRT
<213> ORGANISM: Homo sapiens

<400> SEQUENCE: 9

Asp Ala Glu Phe Arg His Asp Ser Gly Tyr Glu Val His His
1               5                   10

<210> SEQ ID NO 10
<211> LENGTH: 15
<212> TYPE: PRT
<213> ORGANISM: Homo sapiens

<400> SEQUENCE: 10

Asp Ala Glu Phe Arg His Asp Ser Gly Tyr Glu Val His His Gln
1               5                   10                  15

<210> SEQ ID NO 11
<211> LENGTH: 16
<212> TYPE: PRT
<213> ORGANISM: Homo sapiens

<400> SEQUENCE: 11

Asp Ala Glu Phe Arg His Asp Ser Gly Tyr Glu Val His His Gln Lys
1               5                   10                  15

<210> SEQ ID NO 12
<211> LENGTH: 17
<212> TYPE: PRT
<213> ORGANISM: Homo sapiens

<400> SEQUENCE: 12

Asp Ala Glu Phe Arg His Asp Ser Gly Tyr Glu Val His His Gln Lys
1               5                   10                  15

Leu

<210> SEQ ID NO 13
<211> LENGTH: 18
<212> TYPE: PRT
<213> ORGANISM: Homo sapiens

<400> SEQUENCE: 13

Asp Ala Glu Phe Arg His Asp Ser Gly Tyr Glu Val His His Gln Lys
1               5                   10                  15

Leu Val

<210> SEQ ID NO 14
<211> LENGTH: 19

-continued

```
<212> TYPE: PRT
<213> ORGANISM: Homo sapiens

<400> SEQUENCE: 14

Asp Ala Glu Phe Arg His Asp Ser Gly Tyr Glu Val His His Gln Lys
1               5                   10                  15

Leu Val Phe

<210> SEQ ID NO 15
<211> LENGTH: 20
<212> TYPE: PRT
<213> ORGANISM: Homo sapiens

<400> SEQUENCE: 15

Asp Ala Glu Phe Arg His Asp Ser Gly Tyr Glu Val His His Gln Lys
1               5                   10                  15

Leu Val Phe Phe
            20

<210> SEQ ID NO 16
<211> LENGTH: 21
<212> TYPE: PRT
<213> ORGANISM: Homo sapiens

<400> SEQUENCE: 16

Asp Ala Glu Phe Arg His Asp Ser Gly Tyr Glu Val His His Gln Lys
1               5                   10                  15

Leu Val Phe Phe Ala
            20

<210> SEQ ID NO 17
<211> LENGTH: 22
<212> TYPE: PRT
<213> ORGANISM: Homo sapiens

<400> SEQUENCE: 17

Asp Ala Glu Phe Arg His Asp Ser Gly Tyr Glu Val His His Gln Lys
1               5                   10                  15

Leu Val Phe Phe Ala Glu
            20

<210> SEQ ID NO 18
<211> LENGTH: 23
<212> TYPE: PRT
<213> ORGANISM: Homo sapiens

<400> SEQUENCE: 18

Asp Ala Glu Phe Arg His Asp Ser Gly Tyr Glu Val His His Gln Lys
1               5                   10                  15

Leu Val Phe Phe Ala Glu Asp
            20

<210> SEQ ID NO 19
<211> LENGTH: 24
<212> TYPE: PRT
<213> ORGANISM: Homo sapiens

<400> SEQUENCE: 19

Asp Ala Glu Phe Arg His Asp Ser Gly Tyr Glu Val His His Gln Lys
1               5                   10                  15

Leu Val Phe Phe Ala Glu Asp Val
            20
```

<210> SEQ ID NO 20
<211> LENGTH: 25
<212> TYPE: PRT
<213> ORGANISM: Homo sapiens

<400> SEQUENCE: 20

Asp Ala Glu Phe Arg His Asp Ser Gly Tyr Glu Val His His Gln Lys
1               5                   10                  15

Leu Val Phe Phe Ala Glu Asp Val Gly
            20                  25

<210> SEQ ID NO 21
<211> LENGTH: 26
<212> TYPE: PRT
<213> ORGANISM: Homo sapiens

<400> SEQUENCE: 21

Asp Ala Glu Phe Arg His Asp Ser Gly Tyr Glu Val His His Gln Lys
1               5                   10                  15

Leu Val Phe Phe Ala Glu Asp Val Gly Ser
            20                  25

<210> SEQ ID NO 22
<211> LENGTH: 27
<212> TYPE: PRT
<213> ORGANISM: Homo sapiens

<400> SEQUENCE: 22

Asp Ala Glu Phe Arg His Asp Ser Gly Tyr Glu Val His His Gln Lys
1               5                   10                  15

Leu Val Phe Phe Ala Glu Asp Val Gly Ser Asn
            20                  25

<210> SEQ ID NO 23
<211> LENGTH: 28
<212> TYPE: PRT
<213> ORGANISM: Homo sapiens

<400> SEQUENCE: 23

Asp Ala Glu Phe Arg His Asp Ser Gly Tyr Glu Val His His Gln Lys
1               5                   10                  15

Leu Val Phe Phe Ala Glu Asp Val Gly Ser Asn Lys
            20                  25

<210> SEQ ID NO 24
<211> LENGTH: 29
<212> TYPE: PRT
<213> ORGANISM: Homo sapiens

<400> SEQUENCE: 24

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly
            20                  25

<210> SEQ ID NO 25
<211> LENGTH: 30
<212> TYPE: PRT
<213> ORGANISM: Homo sapiens

<400> SEQUENCE: 25

-continued

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala
            20                  25                  30

<210> SEQ ID NO 26
<211> LENGTH: 31
<212> TYPE: PRT
<213> ORGANISM: Homo sapiens

<400> SEQUENCE: 26

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile
            20                  25                  30

<210> SEQ ID NO 27
<211> LENGTH: 32
<212> TYPE: PRT
<213> ORGANISM: Homo sapiens

<400> SEQUENCE: 27

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

<210> SEQ ID NO 28
<211> LENGTH: 33
<212> TYPE: PRT
<213> ORGANISM: Homo sapiens

<400> SEQUENCE: 28

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly

<210> SEQ ID NO 29
<211> LENGTH: 34
<212> TYPE: PRT
<213> ORGANISM: Homo sapiens

<400> SEQUENCE: 29

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu

<210> SEQ ID NO 30
<211> LENGTH: 35
<212> TYPE: PRT
<213> ORGANISM: Homo sapiens

<400> SEQUENCE: 30

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

```
Gly Leu Met
        35

<210> SEQ ID NO 31
<211> LENGTH: 36
<212> TYPE: PRT
<213> ORGANISM: Homo sapiens

<400> SEQUENCE: 31

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val
        35

<210> SEQ ID NO 32
<211> LENGTH: 37
<212> TYPE: PRT
<213> ORGANISM: Homo sapiens

<400> SEQUENCE: 32

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly
        35

<210> SEQ ID NO 33
<211> LENGTH: 38
<212> TYPE: PRT
<213> ORGANISM: Homo sapiens

<400> SEQUENCE: 33

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly
        35

<210> SEQ ID NO 34
<211> LENGTH: 39
<212> TYPE: PRT
<213> ORGANISM: Homo sapiens

<400> SEQUENCE: 34

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val
        35

<210> SEQ ID NO 35
<211> LENGTH: 40
<212> TYPE: PRT
<213> ORGANISM: Homo sapiens

<400> SEQUENCE: 35
```

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
            35                  40

<210> SEQ ID NO 36
<211> LENGTH: 41
<212> TYPE: PRT
<213> ORGANISM: Homo sapiens

<400> SEQUENCE: 36

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile
            35                  40

<210> SEQ ID NO 37
<211> LENGTH: 42
<212> TYPE: PRT
<213> ORGANISM: Homo sapiens

<400> SEQUENCE: 37

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
            35                  40

<210> SEQ ID NO 38
<211> LENGTH: 43
<212> TYPE: PRT
<213> ORGANISM: Homo sapiens

<400> SEQUENCE: 38

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala Thr
            35                  40

<210> SEQ ID NO 39
<211> LENGTH: 6
<212> TYPE: PRT
<213> ORGANISM: Homo sapiens

<400> SEQUENCE: 39

Glu Phe Arg His Asp Ser
1               5

```
<210> SEQ ID NO 40
<211> LENGTH: 5
<212> TYPE: PRT
<213> ORGANISM: Homo sapiens

<400> SEQUENCE: 40

Val Phe Phe Ala Glu
1               5
```